(12) United States Patent
Hartwell et al.

(10) Patent No.: US 12,156,963 B2
(45) Date of Patent: Dec. 3, 2024

(54) NEGATIVE PRESSURE WOUND THERAPY DEVICE STATUS INDICATION USING A CANISTER

(71) Applicant: T.J.Smith and Nephew, Limited, Hull (GB)

(72) Inventors: Edward Yerbury Hartwell, Hull (GB); Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 247 days.

(21) Appl. No.: 17/269,395

(22) PCT Filed: Aug. 15, 2019

(86) PCT No.: PCT/EP2019/071919
§ 371 (c)(1),
(2) Date: Feb. 18, 2021

(87) PCT Pub. No.: WO2020/038822
PCT Pub. Date: Feb. 27, 2020

(65) Prior Publication Data
US 2021/0386925 A1 Dec. 16, 2021

(30) Foreign Application Priority Data
Aug. 21, 2018 (GB) .................................. 1813565

(51) Int. Cl.
*A61M 1/00* (2006.01)
(52) U.S. Cl.
CPC .............. *A61M 1/732* (2021.05); *A61M 1/96* (2021.05); *A61M 1/982* (2021.05); *A61M 1/984* (2021.05);
(Continued)

(58) Field of Classification Search
CPC ........ A61M 1/732; A61M 1/96; A61M 1/982; A61M 1/984; A61M 1/985;
(Continued)

(56) References Cited

U.S. PATENT DOCUMENTS

| 5,408,992 A | * | 4/1995 | Hamlin | ................ | A61B 5/0088 600/109 |
| RE36,434 E | * | 12/1999 | Hamlin | ................ | A61B 5/0088 600/109 |

(Continued)

FOREIGN PATENT DOCUMENTS

| WO | WO-2013034519 A1 | * | 3/2013 | ............ B60Q 3/225 |
| WO | WO-2018030988 A1 | * | 2/2018 | |

OTHER PUBLICATIONS

International Search Report and Written Opinion for Application No. PCT/EP2019/071919, mailed on Nov. 27, 2019, 9 pages.
International Preliminary Report on Patentability for Application No. PCT/EP2019/071919, mailed on Mar. 4, 2021, 8 pages.

*Primary Examiner* — Kai H Weng
*Assistant Examiner* — Alessandro R Del Priore
(74) *Attorney, Agent, or Firm* — Knobbe, Martens, Olson & Bear, LLP

(57) ABSTRACT

Disclosed systems and methods relate to status indication using a canister of negative pressure wound therapy apparatus. A method of providing a visual indication to a user of a negative pressure wound therapy apparatus can include, by a controller of the negative pressure wound therapy apparatus, determining a plurality of conditions associated with provision of negative pressure wound therapy by a negative pressure source of the negative pressure wound therapy apparatus and causing provision of a plurality of visual indications associated with the plurality of conditions to a user and, by at least one light pipe, transmitting light associated with at least one visual indication of the plurality of visual indications through at least a portion of an interior (Continued)

volume of a canister of the negative pressure wound therapy apparatus.

13 Claims, 23 Drawing Sheets

(52) U.S. Cl.
CPC ......... *A61M 1/985* (2021.05); *A61M 2205/15* (2013.01); *A61M 2205/583* (2013.01); *A61M 2205/587* (2013.01)

(58) Field of Classification Search
CPC ........ A61M 2205/15; A61M 2205/583; A61M 2205/587; A61M 2205/18; A61M 2205/3389; A61M 2205/584; A61M 2205/6081; A61M 2209/086
See application file for complete search history.

(56) References Cited

U.S. PATENT DOCUMENTS

| | | | |
|---|---|---|---|
| 8,294,586 B2 | 10/2012 | Pidgeon et al. | |
| 9,415,145 B2* | 8/2016 | Braga | A61M 1/74 |
| 9,682,179 B2 | 6/2017 | May | |
| 2007/0135779 A1 | 6/2007 | Lalomia et al. | |
| 2010/0207768 A1* | 8/2010 | Pidgeon | A61M 1/784 |
| | | | 340/573.1 |
| 2013/0144227 A1 | 6/2013 | Locke et al. | |
| 2014/0303575 A1* | 10/2014 | May | A61M 1/915 |
| | | | 604/319 |
| 2015/0025482 A1* | 1/2015 | Begin | A61M 1/96 |
| | | | 604/319 |
| 2016/0067104 A1* | 3/2016 | Sarangapani | A61M 1/94 |
| | | | 604/290 |
| 2018/0353194 A1* | 12/2018 | Shaffer | A61B 17/22 |
| 2019/0070550 A1* | 3/2019 | Lalomia | A61M 1/63 |

\* cited by examiner

NEGATIVE PRESSURE WOUND THERAPY DEVICE STATUS INDICATION USING A CANISTER

CROSS-REFERENCE TO RELATED APPLICATIONS

This application is a U.S. national stage application of International Patent Application No. PCT/EP2019/071919, filed Aug. 15, 2019, which claims the benefit of U.K. Provisional Application No. 1813565.7, filed Aug. 21, 2018, each of which is hereby incorporated by reference in its entirety.

FIELD

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TNP system.

DESCRIPTION OF RELATED ART

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like.

TNP therapy assists in the closure and healing of wounds by reducing tissue edema, encouraging blood flow, stimulating the formation of granulation tissue, removing excess exudates and may reduce bacterial load. Thus, reducing infection to the wound. Furthermore, TNP therapy permits less outside disturbance of the wound and promotes more rapid healing.

For TNP therapy to be effective, users should be notified of various operating conditions associated with provision of TNP therapy. There exists a need to effectively and reliably notify users of a TNP apparatus of various operating conditions associated with provision of TNP therapy.

SUMMARY

Embodiments disclosed herein are directed to a reduced pressure appliance and methods of treatment using a reduced pressure appliance, and may be useful in the treatment of wounds using reduced pressure.

A negative pressure wound therapy apparatus can include a device housing enclosing a negative pressure source configured to provide negative pressure via a fluid flow path to a wound covered by a wound dressing, and a controller configured to determine a plurality of conditions associated with provision of negative pressure wound therapy by the negative pressure source. The controller can be further configured to cause a provision of a plurality of visual indications associated with the plurality of conditions to a user. A canister can be configured to be attached to the device housing and be fluidically connected to the negative pressure source. The canister can comprise a canister housing including one or more exterior surfaces defining an interior volume configured to store at least some fluid removed from the wound. The one or more exterior surfaces of the canister can be substantially opaque. At least one light pipe can be configured to transmit light associated with at least one visual indication of the plurality of visual indications through at least a portion of the interior volume thereby causing the provision of the at least one visual indication to the user via the canister.

The apparatus of any of the preceding paragraphs can include one or more of the following features. The apparatus can comprise at least one light source that can be supported by the device housing and positioned at least partially on a device housing surface configured to face the interior volume of the canister when the canister is attached to the device housing. A portion of the at least one light pipe can be positioned on a canister surface configured to face the device housing surface. The portion of the at least one light pipe can be positioned in a location of the canister housing surface at least partially coinciding with a location of the light source on the device housing surface when the canister is attached to the device housing.

The apparatus of any of the preceding paragraphs can include one or more of the following features. The apparatus can further comprise of at least one light source that can be a light-emitting diode (LED). The at least one light pipe can be positioned at least partially along the one or more exterior surfaces of the canister. The at least one light pipe can include a plurality of light pipes positioned at least partially along opposing one or more exterior surfaces of the canister. The plurality of conditions can be at least two of normal operation, blockage, canister full, leak, high pressure, or presence of blood. The plurality of visual indications can be at least two of green illumination, yellow illumination, or red illumination.

A negative pressure wound therapy apparatus can include a device housing enclosing, a negative pressure source configured to provide negative pressure via a fluid flow path to a wound covered by a wound dressing, and a controller configured to determine a plurality of conditions associated with provision of negative pressure wound therapy by the negative pressure source. The controller can be further configured to cause a provision of a plurality of visual indications associated with the plurality of conditions to a user. A canister can be configured to be attached to the device housing and be fluidically connected to the negative pressure source. The canister can comprise of a canister housing including one or more exterior surfaces defining an interior volume configured to store at least some fluid removed from the wound. The one or more exterior surfaces of the canister can be substantially opaque. At least one light source positioned in the interior volume of the canister can be configured to be in electrical communication with the controller when the canister is attached to the device. The at least one light source can further be configured to provide at least one visual indication of the plurality of visual indications to the user via the canister.

The apparatus of any of the preceding paragraphs can include one or more of the following features. The apparatus can include at least one light source that can be positioned at least partially on a surface of the canister. The at least one light source can be positioned at least partially on a portion of a substantially transparent surface of the canister. The substantially transparent surface of the canister can be a polished surface. The apparatus can further comprise at least one electrical connection positioned along the one or more exterior surfaces of the canister or in the interior volume of the canister, the at least one electrical connection configured to provide electrical communication between the at least one light source and the controller. The light source can be a LED. The plurality of conditions can be at least two of normal operation, blockage, canister full, leak, high pressure, or presence of blood. The plurality of visual indications can be at least two of green illumination, yellow illumination, or red illumination. The device housing can include a first connector positioned on an exterior surface of the device housing. The canister housing can include a second connector positioned on an exterior surface of the canister housing. When the canister is attached to the device, the first and second connectors can complete an electrical circuit configured to facilitate electrical communication between the at least one light source and the controller. The first connector can be positioned on a bottom exterior surface of the device housing. The second connector can be positioned on a top exterior surface of the canister housing.

A method of providing a visual indication to a user of a negative pressure wound therapy apparatus that can comprise, by a controller, determining a plurality of conditions associated with provision of negative pressure wound therapy by a negative pressure source of the negative pressure wound therapy apparatus and causing a provision of a plurality of visual indications associated with the plurality of conditions to a user. The method can also comprise transmitting by at least one light pipe at least one visual indication of the plurality of visual indications through at least a portion of an interior volume of a canister of the negative pressure wound therapy apparatus.

The method of any of the preceding paragraphs can include one or more of the following features. The method can further comprise generating, by a light source, light associated with the at least one visual indication. The interior volume of the canister can be defined by one or more exterior surfaces of the canister, the one or more exterior surfaces of the canister being substantially opaque. The at least one light pipe can be positioned at least partially along the one or more exterior surfaces of the canister. The at least one light pipe can include a plurality of light pipes positioned at least partially along opposing one or more exterior surfaces of the canister. The plurality of conditions can be at least two of normal operation, blockage, canister full, leak, high pressure, or presence of blood. The visual indications can be at least two of green illumination, yellow illumination, or red illumination.

A method of providing a visual indication to a user of a negative pressure wound therapy apparatus that can comprise, by a controller, determining a plurality of conditions associated with a provision of negative pressure wound therapy by a negative pressure source of the negative pressure wound therapy apparatus and causing a provision of a plurality of visual indications associated with the plurality of conditions to a user. The method can also comprise, by at least one light source positioned in an interior volume of a canister of the negative pressure wound therapy apparatus, providing at least one visual indication of the plurality of visual indications.

The method of any of the preceding paragraphs can include one or more of the following features. The at least one light source can be positioned at least partially on one or more of: a surface of the canister or a portion of a substantially transparent surface of the canister. The substantially transparent surface of the canister can comprise of a polished surface. The at least one light source can be positioned at least partially on a portion of a substantially transparent surface of the canister. The substantially transparent surface of the canister can be a polished surface. The plurality of conditions can be at least two of normal operation, blockage, canister full, leak, high pressure, or presence of blood. The plurality of visual indications can be at least two of green illumination, yellow illumination, or red illumination. The method can include facilitating electrical communication between the controller and the at least one light source via an electrical circuit completed by a first connector positioned on an exterior surface of a housing of the negative pressure wound therapy apparatus and a second connector positioned on an exterior surface of the canister. The electrical circuit can be completed when the canister is connected to the housing of the negative pressure wound therapy apparatus. The first connector can be positioned on a bottom exterior surface of the housing of the negative pressure wound therapy apparatus. The second connector can be positioned on a top exterior surface of the canister.

BRIEF DESCRIPTION OF THE DRAWINGS

Features and advantages of the present disclosure will be apparent from the following detailed description, taken in conjunction with the accompanying drawings of which.

DETAILED DESCRIPTION

Figure 1:
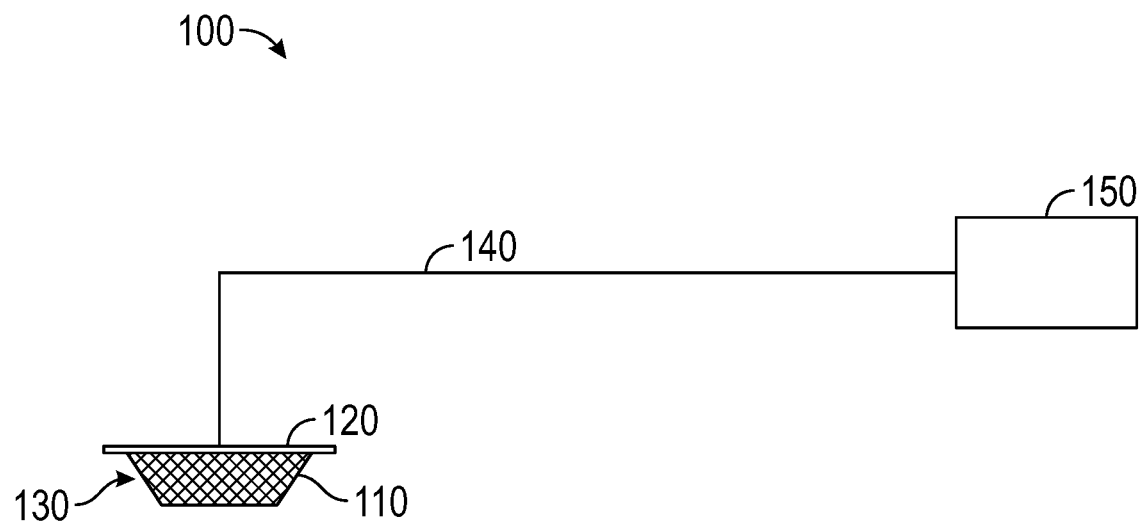
FIG. 1 illustrates a reduced pressure wound therapy system according to some embodiments.

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds, and abdominal wounds or the like.

TNP therapy can assist in the closure and healing of wounds by reducing tissue oedema, encouraging blood flow, stimulating the formation of granulation tissue, removing excess exudates, and reducing bacterial load. Thus reducing infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760−X) mmHg In addition, negative pressure that is "less" or "smaller" than −X mmHg corresponds to pressure that is closer to atmospheric pressure (for example, −40 mmHg is less than −60 mmHg). Negative pressure that is "more" or "greater" than −X mmHg corresponds to pressure that is further from atmospheric pressure (for example, −80 mmHg is more than −60 mmHg).

Overview

Negative pressure wound therapy (NPWT) systems can detect various operating conditions and indicate such conditions to users, such as the patient or medical professional. The operating conditions can include system on/off, standby, pause, normal provision of negative pressure wound therapy, leak in a fluid flow path, blockage in the fluid flow path, canister full, high pressure or overpressure, blood detected in the fluid flow path, low power, system error, or any other similar or suitable conditions or combinations thereof NPWT systems can include one or more of visual, audible, tactile, haptic, or other types of indicators or alarms configured to signal to the user various operating conditions. The indicators or alarms can include speakers, displays, light sources, vibrating elements, or combinations thereof. Provision of alarms or alerts can be guided by one or more applicable standards, such as the IEC 60601-1-8 standard for medical equipment alarms or alerts.

For example, IEC 60601-1-8 standard provides that, in some cases, visual alerts generated by an NPWT system should be correctly perceived at a distance of at least 4 meters from the system. In some cases, NPWT system should generate high, medium, and low priority (or informational) alerts. According to the IEC 60601-1-8 standard, alerts of different priorities should be of different color, such as red, yellow, and cyan (or yellow) respectively. For example, NPWT system can emit a cyan-colored visual indication to indicate normal operation, a yellow-colored visual indication to provide a warning (or medium priority alert), such as leakage, blockage, or the like, or emit red-colored indication to provide a high priority alert, such as overpressure, blood detected in the fluid flow path, or the like. The IEC 60601-1-8 standard includes further requirements for flashing visual alerts of various priorities.

A NPWT system can provide visual indication of various alerts or operating conditions using a canister. The NPWT system can light up the canister to indicate a particular operating condition to a user. Such NPT system can provide the user with simple, reliable, and accurate feedback regarding operation of the device.

In the description below, examples use, but are not limited to, light emitting diodes (LEDs) as visual signal devices. NPWT systems can use a super bright SMTL4 LED manufactured by BIVAR. In some cases, light sources or visual signal devices can be one or more of LEDs, organic LEDs (OLEDs), fluorescent based lights, laser lights, luminescent backlights (such as electro-luminescent back panel of OLED panel), or the like. The visual signal devices can be, but are not limited to, red, yellow, green, cyan, blue, purple, orange, or any color combination thereof.

The visual signal devices can be built into a housing that enclosed the negative pressure source. The visual signal devices can be placed in multiple areas or in multiple alternate positions on the surface of the housing that comes into contact with the canister, such as a single visual device in the bottom center surface of the housing or multiple visual signal devices on the edges of the bottom surface of the housing. Light guides or light pipes can be used to transmit the light from the visual signal devices into the canister of the device. In some cases, the canister can glow with particular colors or color combinations to alert the user to one or more operating conditions of the NPWT system.

Visual signal devices can be built into the canister. The visual signal devices can be placed in multiple areas or in multiple alternate positions on the canister such as the bottom or the sides of the canister.

In some cases, the canister can additionally be polished to diffuse the light or additionally aid in desired light transmission and refraction. For example, the interior surfaces of the canister can be polished. The polishing can create a homogenous glow. The exterior surfaces of the canister can be frosted to aid in obscuring the contents of the canister. Illumination produced by the light can additionally or alternatively aid for readability of the canister fill lines, which allows more accurate determinations of the status of the canister.

Negative Wound Pressure Therapy System

FIG. 1 illustrates a negative or reduced pressure wound treatment system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected to the wound cover 120 with a reduced pressure wound therapy assembly 150 configured to supply reduced pressure. The wound cover 120 can be in fluidic communication with the wound cavity 110. The assembly 150 can be a canisterless assembly (meaning that exudate is collected in the wound dressing or is transferred via tube 140 for collection to another location). However, any of the assemblies disclosed herein can be configured to include or support a canister. Additionally, in any of the systems disclosed herein, any of the assemblies can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

The wound cover 120 can have a port (not shown) configured to receive an end of the conduit 140. The port can be Renays Soft Port available from SMITH & NEPHEW. The conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the assembly 150 and the wound cover 120, so as to supply the reduced pressure provided by the assembly 150 to wound cavity 110.

The wound cover 120 and the wound filler 130 can be provided as a single article or an integrated single unit. No wound filler can also be possible and the wound cover by itself may be considered the wound dressing. The wound dressing can then be connected, via the conduit 140, to a source of negative pressure, such as the assembly 150. The assembly 150 can be miniaturized and portable, although larger conventional negative pressure sources can also be used.

The wound cover 120 can be located over a wound site to be treated. The wound cover 120 can form a substantially sealed cavity or enclosure over the wound site. The wound cover 120 can be configured to have a film having a high water vapor permeability to enable the evaporation of surplus fluid, and can have a super absorbing material contained therein to safely absorb wound exudate. It will be appreciated that throughout this specification reference is made to a wound. In this sense, it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

The system can be designed to operate without the use of an exudate canister. The system can be configured to support an exudate canister. Configuring the assembly 150 and tubing 140 can be done so that tubing 140 can be quickly and easily removed from the assembly 150 and can facilitate or improve the process of dressing or assembly changes, if necessary. Any of the embodiments disclosed herein can be configured to have any suitable connection between the tubing and the assembly 150.

The assembly 150 can be configured to deliver negative pressure of approximately −80 mmHg, or between about −20 mmHg and 200 mmHg in some implementations. The pressure range can be between about −40 mmHg and −150 mmHg Alternatively, a pressure range of up to −75 mmHg, up to −80 mmHg or over −80 mmHg can be used. Also a pressure range of below −75 mmHg can be used. Alternatively, a pressure range of over approximately −100 mmHg, or even 150 mmHg, can be supplied by the assembly 150.

In operation, the wound filler 130 is inserted into the wound cavity 110 and wound cover 120 is placed so as to seal the wound cavity 110. The assembly 150 provides a source of a negative pressure to the wound cover 120, which is transmitted to the wound cavity 110 via the wound filler 130. Fluid (e.g., wound exudate) is drawn through the conduit 140, and can be stored in a canister. Fluid can be absorbed by the wound filler 130 or one or more absorbent layers (not shown).

Wound dressings that can be utilized with the disclosed embodiments include Renasys-F, Renasys-G, Renasys AB, and Pico Dressings available from SMITH & NEPHEW. Further description of such wound dressings and other components of a negative pressure wound therapy system that can be used with any of the disclosed embodiments are found in U.S. Patent Publication Nos. 2011/0213287, 2011/0282309, 2012/0116334, 2012/0136325, 2013/0110058, and 2016/0184496 and U.S. Pat. Nos. 8,843,327 and 9,737,649, which are incorporated by reference in their entirety. Other suitable wound dressings or NPWT systems can be utilized.

Status Indications Using Canisters

Figure 2A:
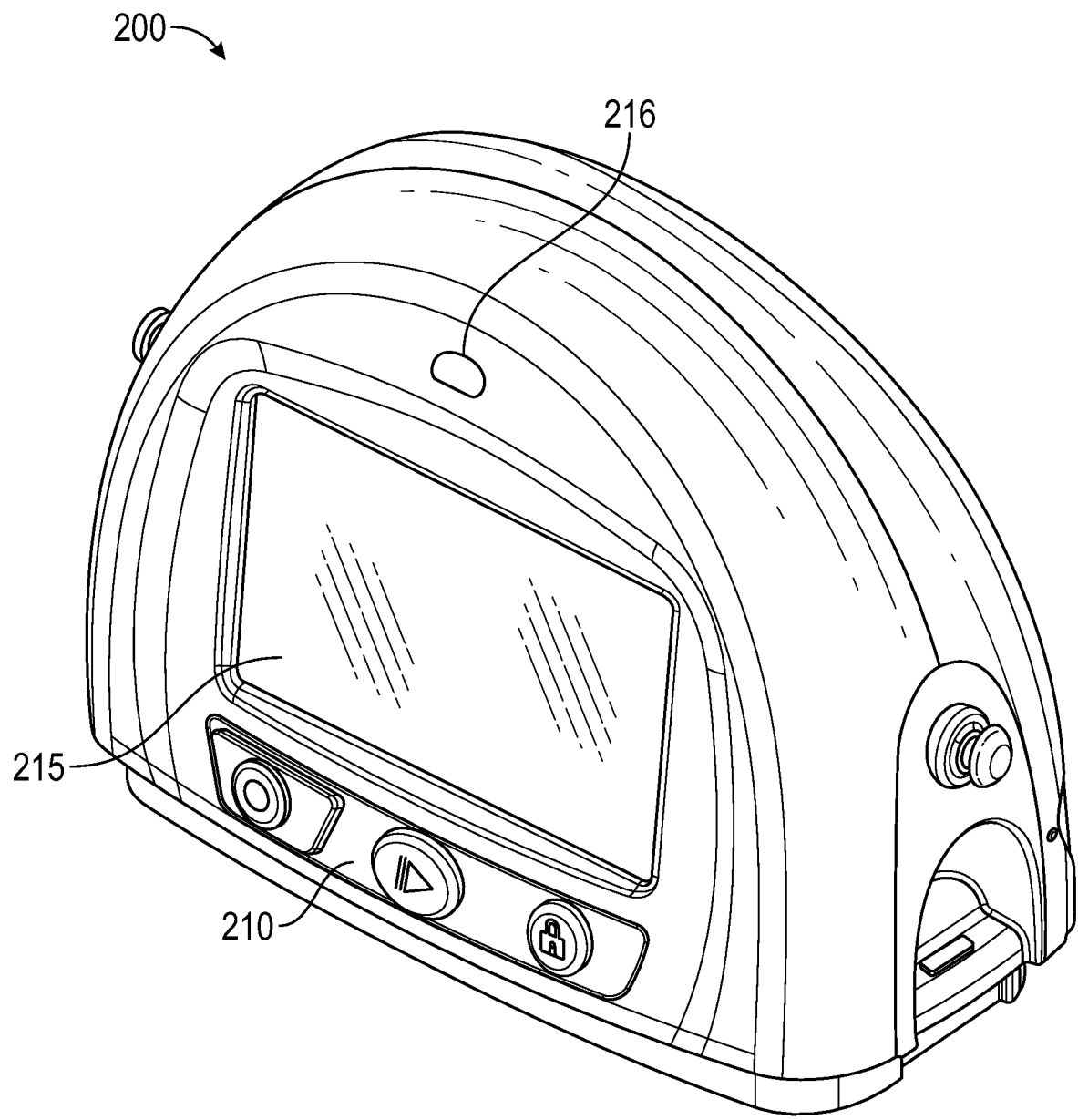
FIG. 2A-2D illustrate reduced pressure wound therapy devices according to some embodiments.

FIG. 2A illustrates a front-top view of the negative pressure device housing 200. The device housing 200 encloses a negative pressure source configured to provide negative pressure via a fluid flow path to a wound covered by a wound dressing, and a controller configured to determine a plurality of conditions associated with provision of negative pressure wound therapy by the negative pressure source, the controller further configured to cause provision of a plurality of visual indications associated with the plurality of conditions to a user. Interface buttons 210 can be used to control provision of negative pressure wound therapy by the NPWT system. Display 215 can guide the user through various screens, menus, or the like to operate the system. Visual indicator 216 can convey one or more alerts to the user.

Figure 2B:
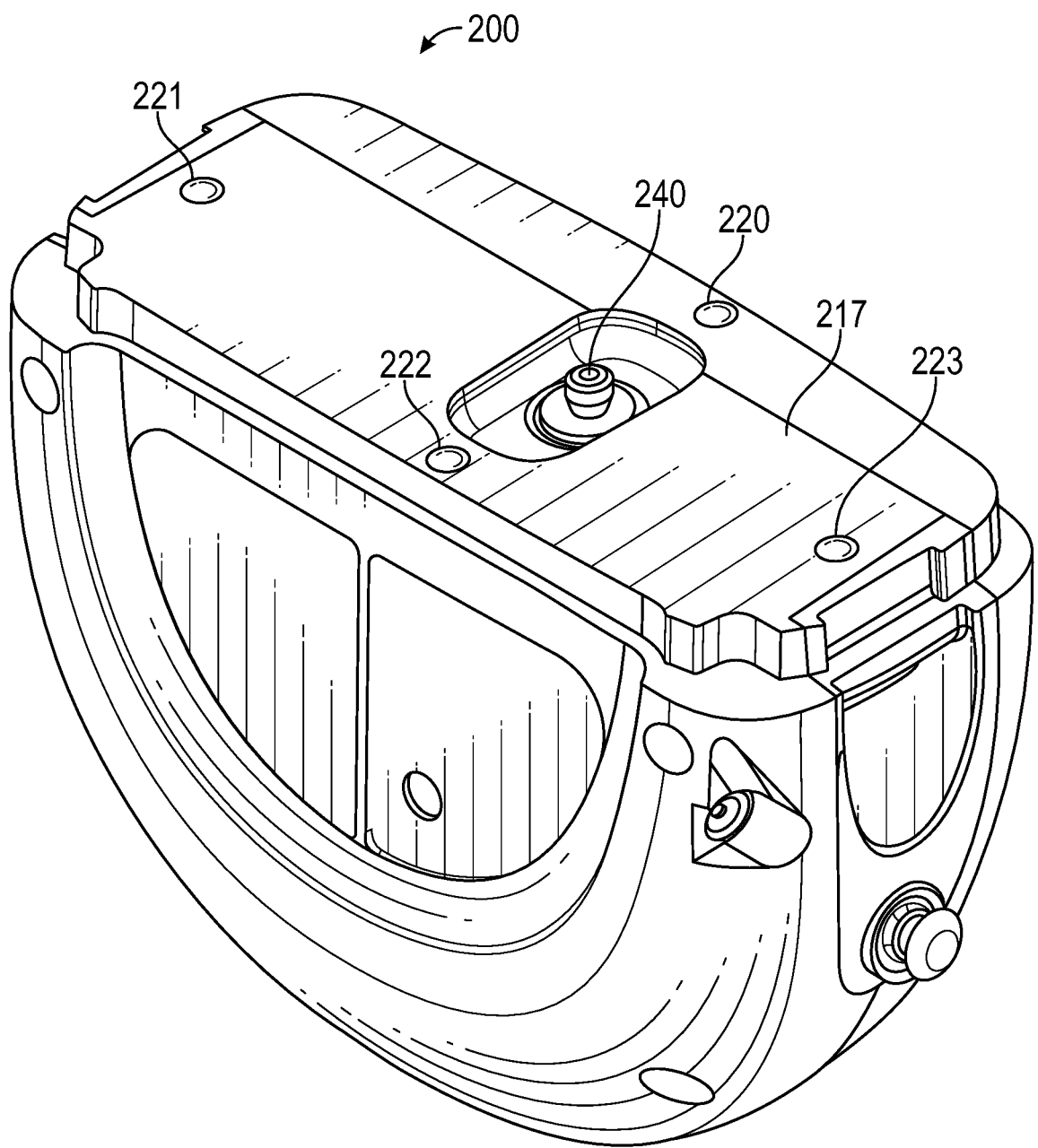
Figure 2C:
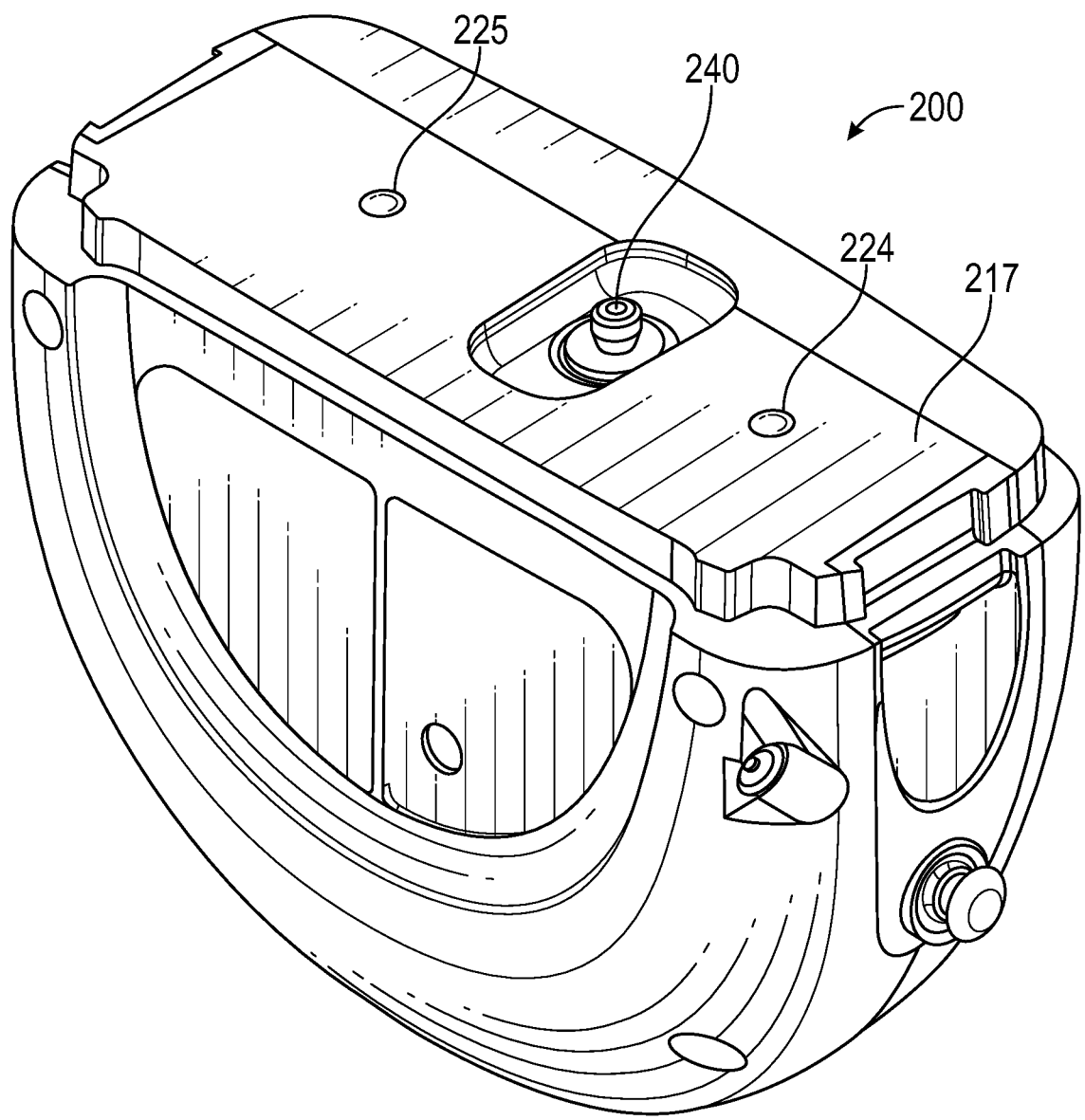
Figure 2D:
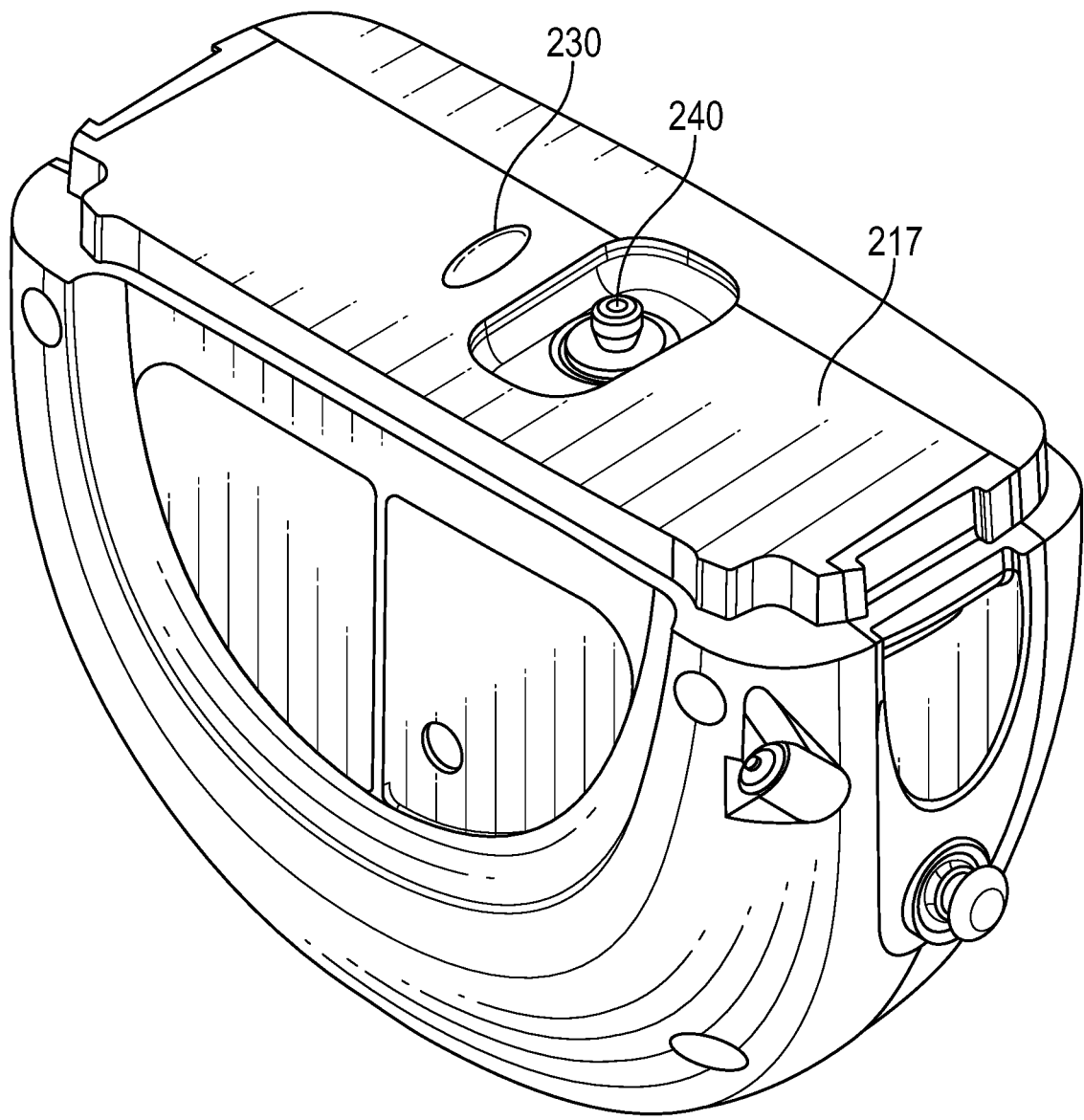

FIGS. 2B-2D show bottom-rear views of the device housing 200. FIG. 2B illustrates that one or more light sources 220, 221, 222, 223, such as LEDs, luminescent backlights, OLEDs, or the like, can be placed on the four edges of the bottom surface 217 of the device housing 200 surrounding the negative pressure port 240. The light sources 220, 221, 222, 223 can be same or a combination of different types of light sources. FIG. 2C illustrates the one or more light sources 224, 225 can be placed in the midline of the bottom surface 217 near the negative pressure port 240. FIG. 2D illustrates a single light source 230 placed near the negative pressure port 240 on the bottom surface 217. Uses of the single light source 230 can require a strong intensity light source, however all types of light sources with different intensities can be used in all types of configurations. While FIGS. 2B-2D illustrate some example of light source placement, other alternative or additional light source placements can be used.

In some cases, one or more lights sources can use colors such as, but are not limited to, red, yellow, green, blue, purple, orange, or any color combination thereof. The one or more light sources can be turned on and off in sequences to indicate operation or device status. For example, the four light sources illustrated in FIG. 2B can be turned on and off in a clockwise or counterclockwise sequence, linear sequence, only two of the light sources may be turn one, or the like. The different hues of the visual signal devices can function as a user interface by indicating the status of the device and the status of the user. Suitably shaped light sources can be used, such as rounded LEDs or flat LEDs.

In some cases, one or more light sources, such as the one or more light sources 220, 221, 222, 223, can be activated at all at once, in groups (such as pairs), individually, or the like. The one or more light sources can flash at same or different frequencies. The one or more light sources can individually flash different colors, flash same color, or groups of light sources can flash different colors. The one or more light sources can flash colors according to a sequence, patterns, duration, color, or the like. For example, the light source can be flashed in the following sequence: 220, 223, 222, and 221; 220, 222, 223, and 221; or the like.

In some cases, one or more light sources can have three possible states, such as green (solid or flashing), yellow (solid or flashing), or red (solid or flashing). One or more light sources can additionally or alternatively have states that vary or are modulated based on detected status of the NPWT system, user, or the like. For example, one or more states of one or more light sources can be modulated by detected user's heartbeat, respiration rate, or the like. In some cases, solid green can indicate that the NPWT system is operating as expected. Flashing green can indicate that there are no urgent warnings and that therapy is active. Such indications can be used when the battery is low or when the end of product life is expected to be reached soon. The flashing green indication can indicate to a user that whilst the NPWT system is operating in an acceptable fashion at present, there may be action required if therapy is to be continued. A red indication can indicate therapy failure, such as presence of blood in the fluid flow path, overpressure, or the like. A yellow indication can be generated to indicate a low priority alert.

A canister can be configured to be attached to the device housing and further configured to be fluidically connected to the negative pressure source. For example, the canister can be attached using clips illustrated in FIGS. 3A-3C and described in more detail U.S. Pat. No. 8,622,981, which is incorporated by reference in its entirety, or other suitable attachment mechanisms. The canister can comprise a canister housing including one or more exterior surfaces defining an interior volume configured to store at least some fluid removed from the wound wherein the one or more exterior surfaces of the canister can be substantially opaque. The light transmitted from light source can thereby be transmitted to serve as an indication to the user via the canister.

Figure 3A:
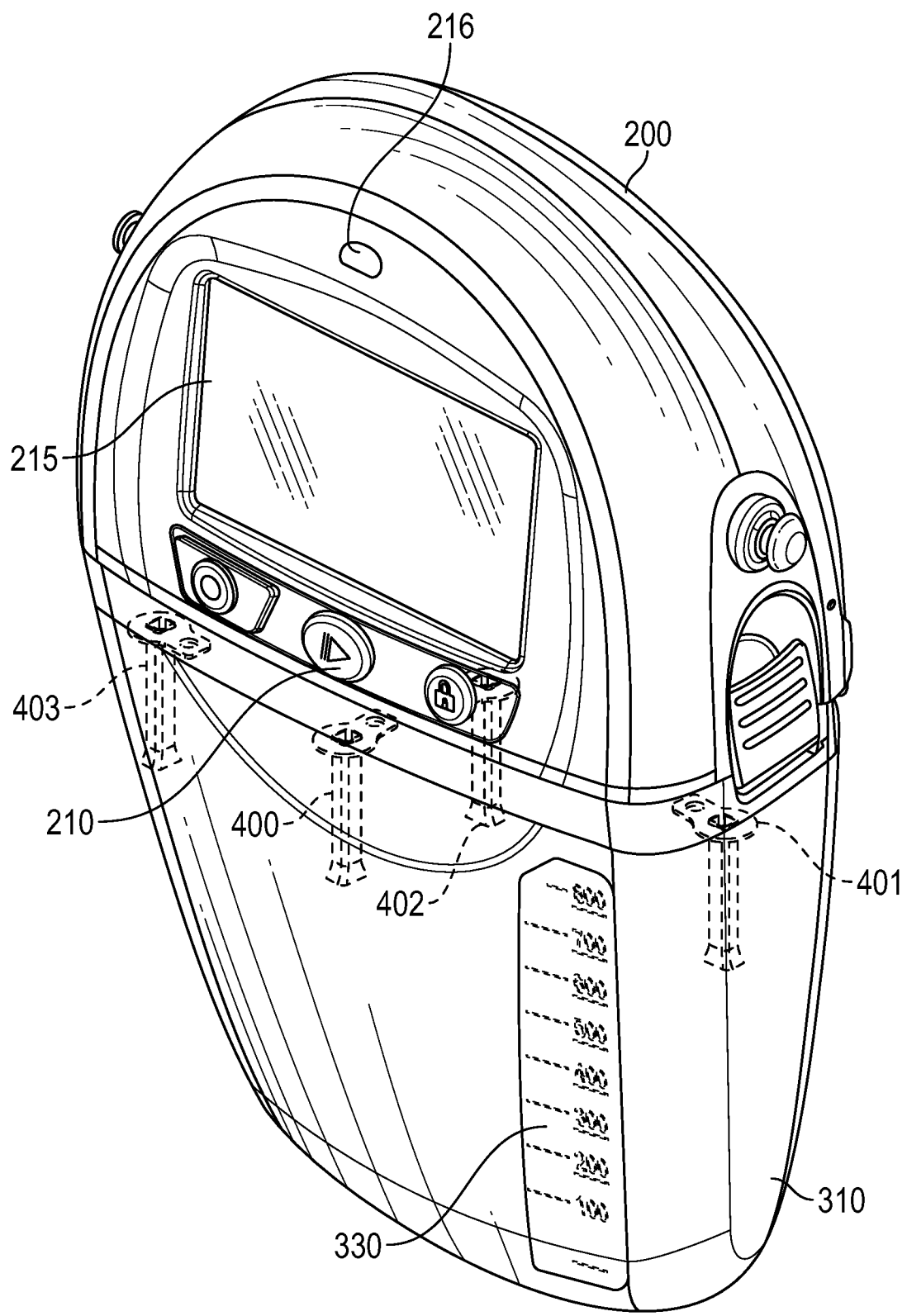
FIG. 3A-3C illustrate reduced pressure wound therapy devices attached to canisters according to some embodiments.
Figure 3B:
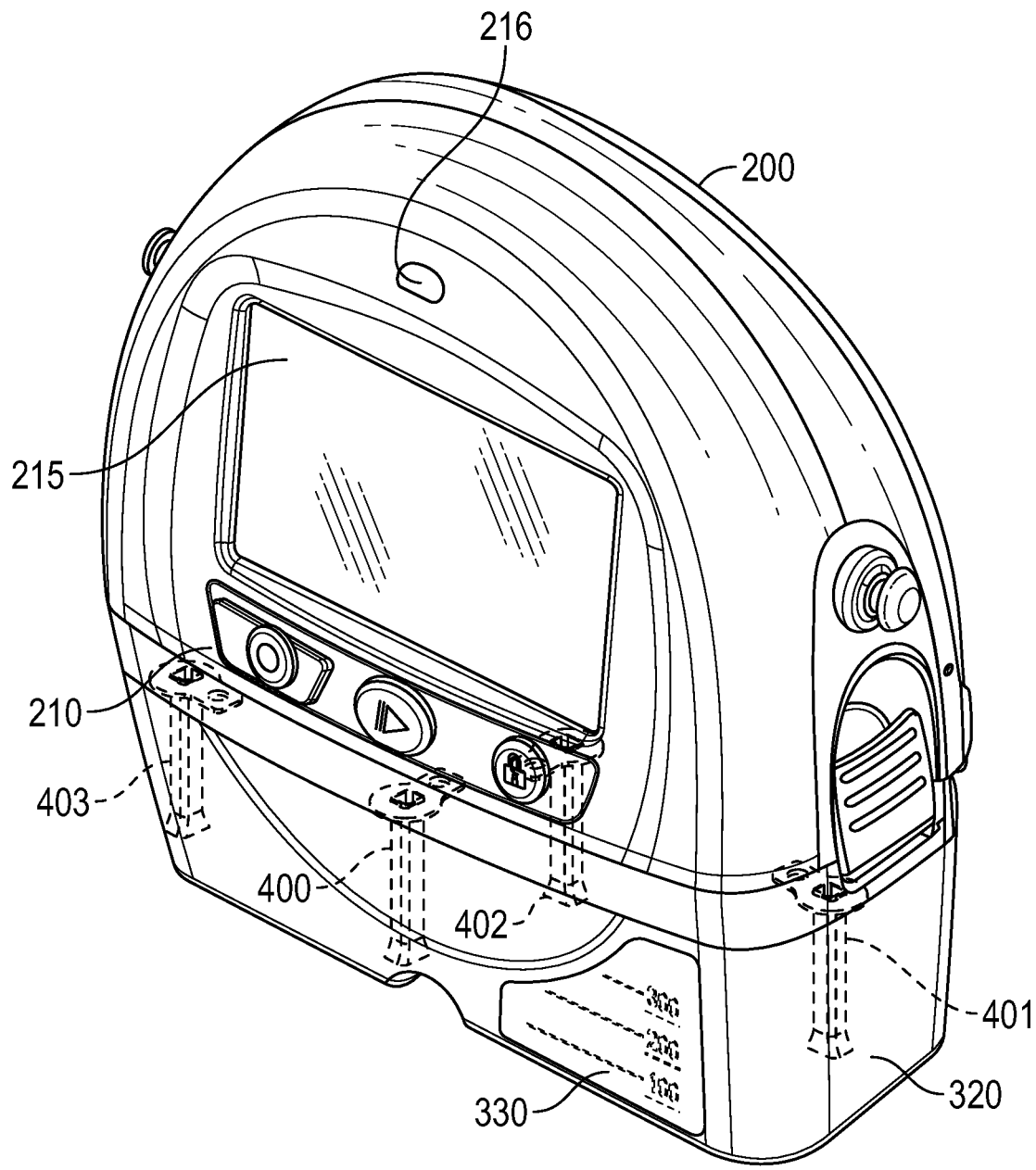
Figure 3C:
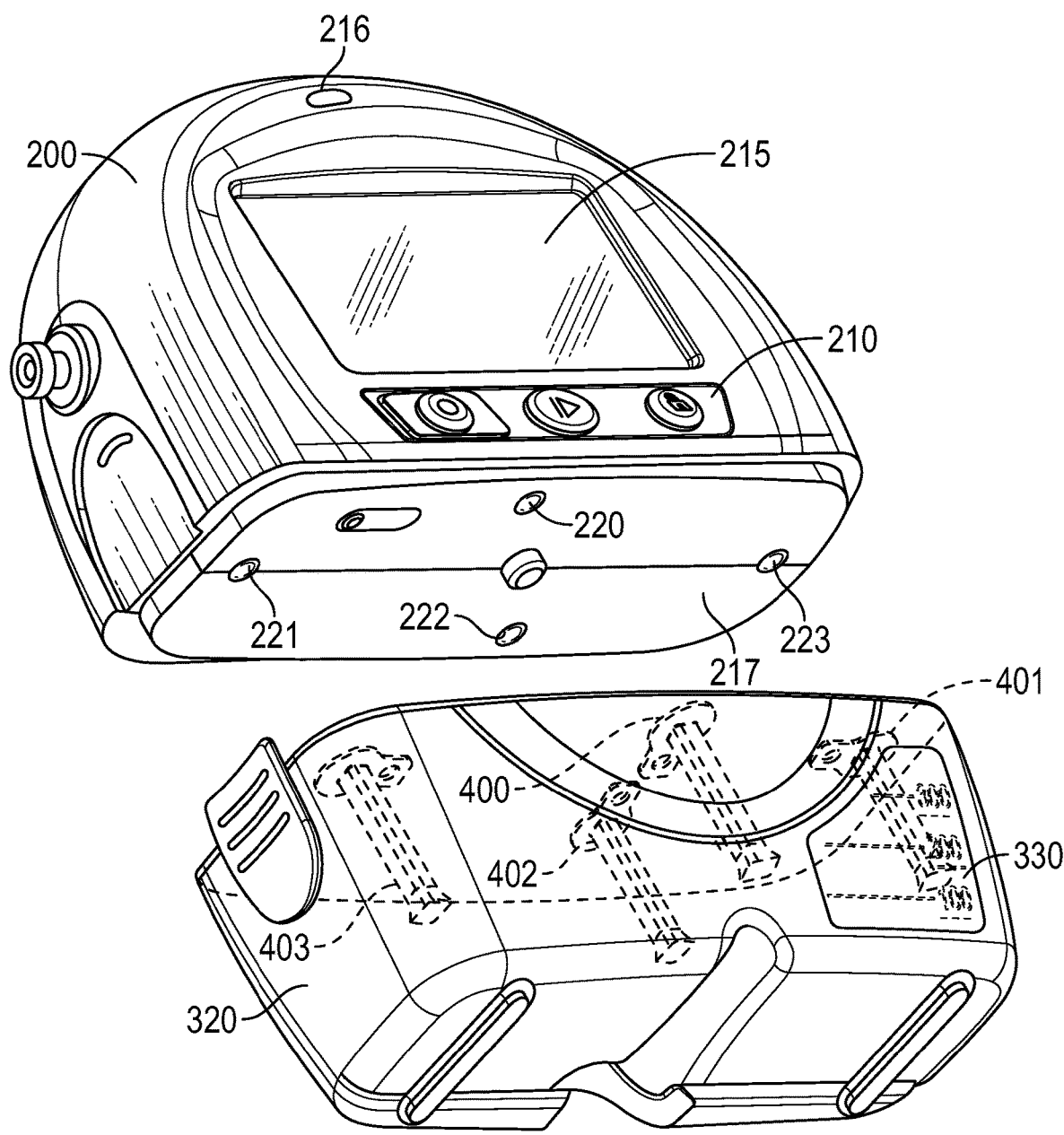

FIGS. 3A and 3B show the device housing 200 attached to canisters. FIG. 3A illustrates the device housing 200 connected to a large canister 310, such as 800 mL canister. FIG. 3B illustrates the device housing 200 connected to a small canister 320, such as 300 mL canister. Other sizes and alternative canister shapes can be used. As is illustrated in FIGS. 3A-3B and FIG. 3C, the canister can be attached to the bottom surface 217 of the device housing 200. The canister can include a housing with exterior surfaces that define an interior volume in which fluid removed from the wound is stored.

One or more light guides or light pipes 400, 401, 402, 403 can protrude into the canister 310, 320. The light pipes can be the same types or can be a combination of different types of light pipes. One or more light pipes can transmit light generated by one or more light sources mounted on the bottom surface 217 (or another suitable surface), such as one or more light sources 220, 221, 222, 223 into another portion or location in the canister. For example, one or more light pipes can transmit the generated light into the canister so that the entire or substantially entire surface of the canister lights up to provide one or more visual indications to the user. In some cases, lights pipes can transmit the light to each of the side surfaces of the canister and the bottom surface of the canister. In some cases, multiple light pipes can be used to transmit light to multiple locations on larger surfaces of the canister.

The one or more light pipes can be located on the canister-device interface. The one or more light pipes can be positioned at least partially along the one or more exterior surfaces of the canister housing. For example, the one or more light pipes can be positioned in the interior volume of the canister along the one or more exterior surfaces. The one or more light pipes can comprise a plurality of light pipes positioned at least partially along opposing one or more exterior surfaces of the canister. The one or more light pipes can additionally or alternatively include optical diffusers to scatter the light on the sidewalls of the canister. The one or more light pipes can additionally or alternatively connect directly with the sidewalls to prevent the exudate obscuring the light. The one or more light pipes positioned near the canister fill lines (for example, 330 as described herein) can change colors or flash different sequences based on level of exudate in the canister. For example, the one or more light pipes can be pulsed in green color when the canister is determined to be less than 75% full, fast flash amber when the canister is determined to be up to 95% full, or be in solid red when the canister is determined to be more than 95% full. In some cases, other colors, flash or solid sequences, or canister fill levels can be used.

As is illustrated in FIGS. 3A-3B, fill lines 330 can be shown on the side of the canister to indicate the amount of fluid in the canister. Lighting up the canister as described herein can assist with readability of the fill lines. The fill lines 330 can be located on other areas of the canister such as the back and sides as well.

The canisters 310 or 320 can be frosted on the outside to obscure vision of the content of the canister. The canisters 310 or 320 can be polished on the inside or in the interior volume to better direct the light transmission and achieve desired illumination of the canister, such as achieving a homogenous glow. The external surface of the canister can be frosted to act as a light diffuser. One or more light sources, such as the one or more of light sources 220-221, can be recessed within the device housing 200 to prevent light leakage. One or more light pipes, such as the one or more of light pipes 400, 401, 402, 403 can project or protrude from the surface of the canister to engage with the one or more recessed light sources in the device.

FIG. 3C shows how a canister, such as the canister 320, interfaces with the device housing 200. As illustrated, the bottom surface 217 of the device housing is placed in contact with top surface of the canister 320 when the canister is attached to the device housing 200. The large canister 310 can similarly be attached to the device housing 200. As illustrated, the one or more light pipes 400, 401, 402, or 403 can be positioned to at least partially coincide with the one or more locations of the one or more light sources, such as the one or more light sources 220, 221, 222, 223, positioned on the bottom surface 217 of the device housing. As shown in FIG. 3C, each of the light sources 220, 221, 222, 223 align with light entrance portion of the respective light pipe. Corresponding light pipe arrangements reflecting lights source placements illustrated in FIG. 2B-2D can also be used.

In some cases, proper placement or engagement of the canister to the device can be detected. For example, any one or more of the light sources 220-223 can include a detector, such as a photo sensor, that can detect that one or more of corresponding light pipes are engaged. For instance, the detector can determine if the corresponding light pipe is positioned within at least a threshold distance or orientation. The one or more detectors can be coupled to a processor or controller that can determine proper engagement of the canister. If it is determined the canister is properly engaged, the controller can cause the negative pressure source to provide negative pressure wound therapy. If it is determined that the canister is not properly engaged the controller can prevent the negative pressure source from operating. When the canister is determined to be engaged, one or more of the light sources can flash colors or sequences to indicate that the canister is engaged. When the canister is determined to not be engaged, one or more light sources can flash different colors or sequences to indicate that the canister is not engaged.

In some cases, type of the canister (such as small or large) can be similarly determined or indicated. For example, the canister can guide light to a particular detector dependent on its type. As another example, one or more detectors can be placed at different locations on the bottom surface 217 of the device to detect the canister type.

Figure 4:
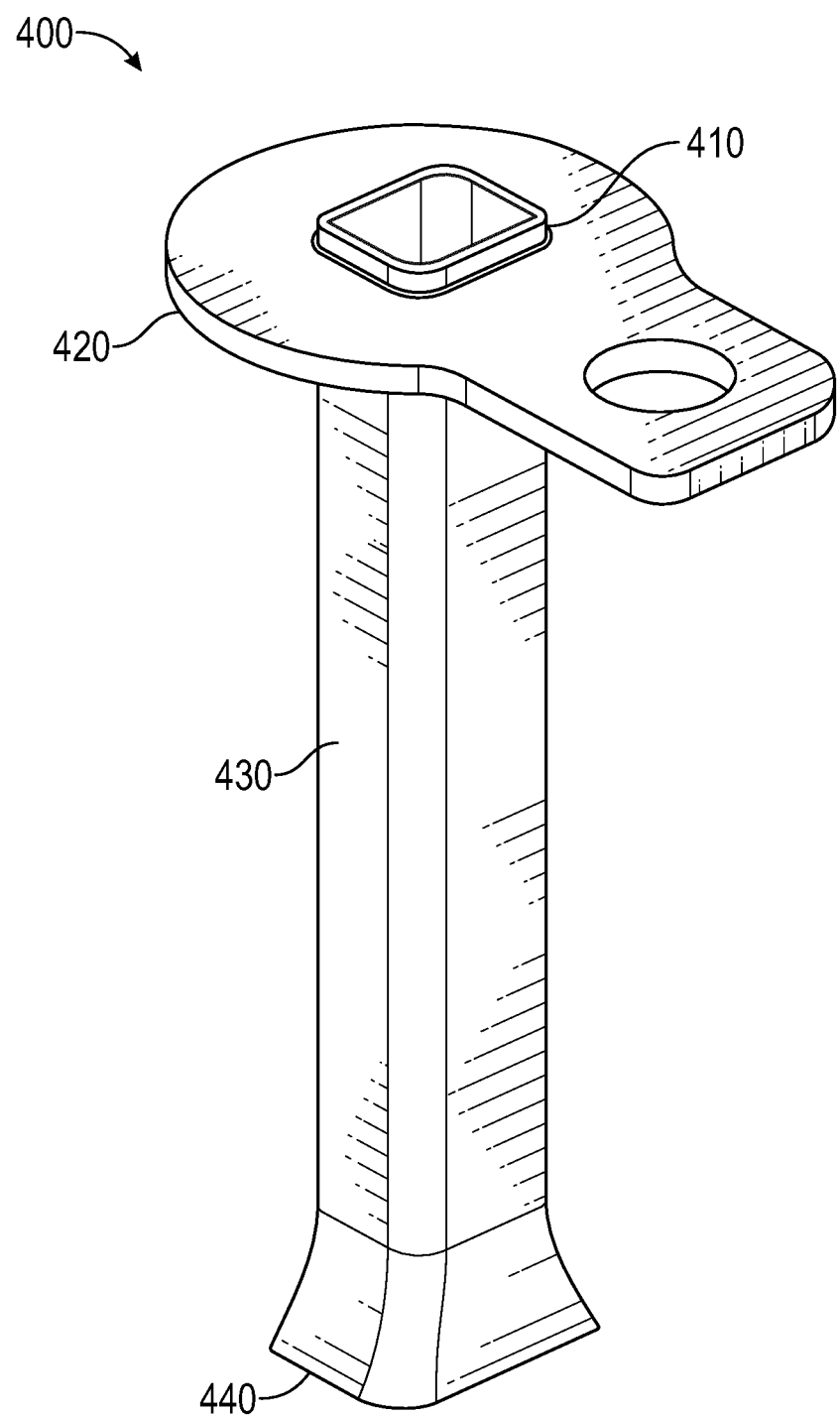
FIG. 4 illustrates a light pipe according to some embodiments.

FIG. 4 shows a light pipe that can be used to transmit the light from a light source, such as 220, 221, 222, 223, into the canister. The illustrated light pipe can be any of the light pipes described herein, such as the light pipe 400. Transmission can involve one or more of transport or distribution. The light pipe can emit approximately the same brightness as a light source and can minimize light lost. The light source can be effectively matched with the entrance of the light pipe to minimize light loss. Effective light pipe and light source matching can occur when the light source radiation pattern angle matches the acceptance pattern angle of the light pipe. The light pipe can provide uniform illumination, reduced shadowing and glare, design flexibility, and interchangeable installation. The light pipe can be either rigid or flexible. A rigid design can be produced with a hard plastic material or metal material that will have a vertical or right angle construction that can direct light with a minor loss in intensity. A flexible design can be made with optical grade plastics. The light pipe can be solid or hollow. The flexible design can make subtle angles that allow ease of integration around existing components of a system. Customizable light pipes can be used. For example, the light pipe can be designed using ray tracing that uses CAD/CAM models that can ensure proper design and optimal light transmittance. Ray tracing can use a CAD/CAM software to create a model and use an artificial light source, such as an LED or an emitting disc, to simulate visual signal intensity. A detector plane can be used and can be placed in front of a surface where the light is intended to exit. The simulated light can then be measured to determine the optimal visual signal source placement and light pipe design. The light pipe can have a vertical or right angle design. The light pipe can be a single unit or a multiple unit and can come in variety of shapes, such as round or rectangular. A multi-unit light pipe can be designed to prevent light bleeding between adjacent light pipes. A light pipe can be designed to optically to shine as required for a particular application.

The illustrated light pipe can be located on the surface of the canister that faces the device housing when canister is attached to the device housing. The light pipe can provide a pathway for the light from the light source into the canister. The light pipe can include a light entrance 410 which is contoured to closely match the outer surface of the light source, such as an LED. In this way, the body 430 of the light pipe can be brought into intimate proximity with the light source. The light pipe can flare outwardly in a substantially thrusted conical fashion. The light pipe 400 can include a fixing region or portion 420 which permits the light pipe to be secured on the canister, such as on top surface of the canister as describe herein. The portion 420 can include a hole for a screw or another type of attachment device. The portion 420 can be molded integral to the canister or can be welded to the canister. Some canisters can have removable or interchangeable light pipes and utilize the fixing region 420 to attach or anchor to the canister. An upper light entrance 410 of the light pipe can be substantially cylindrical. The light pipe can include a light emitting exit portion 440 which emits light through the canister as to provide a reliable, effective visual indication to the user. The exit portion 440 can have an outwardly flared design to maximize light transmission. Light pipes can be in different shapes to transmit light to different areas of the canister. Light pipes can be removable and some designs of the canisters allow custom movable placement of light pipes. Light pipe can be of any suitable length depending on the canister size, shape, or the like.

Figure 5A:
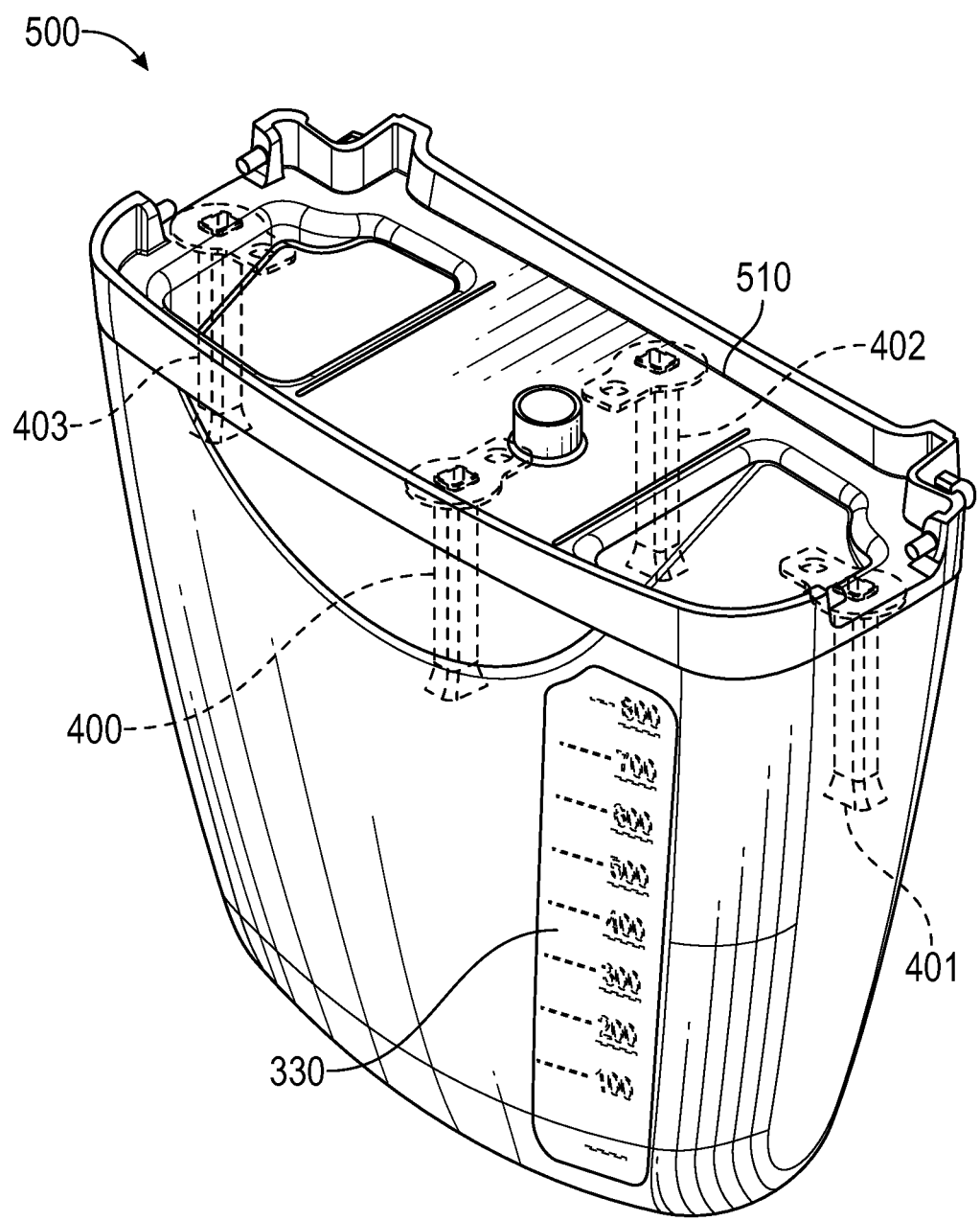
FIGS. 5A-5E and 6A-6E illustrate canisters with light pipes according to some embodiments.
Figure 5B:
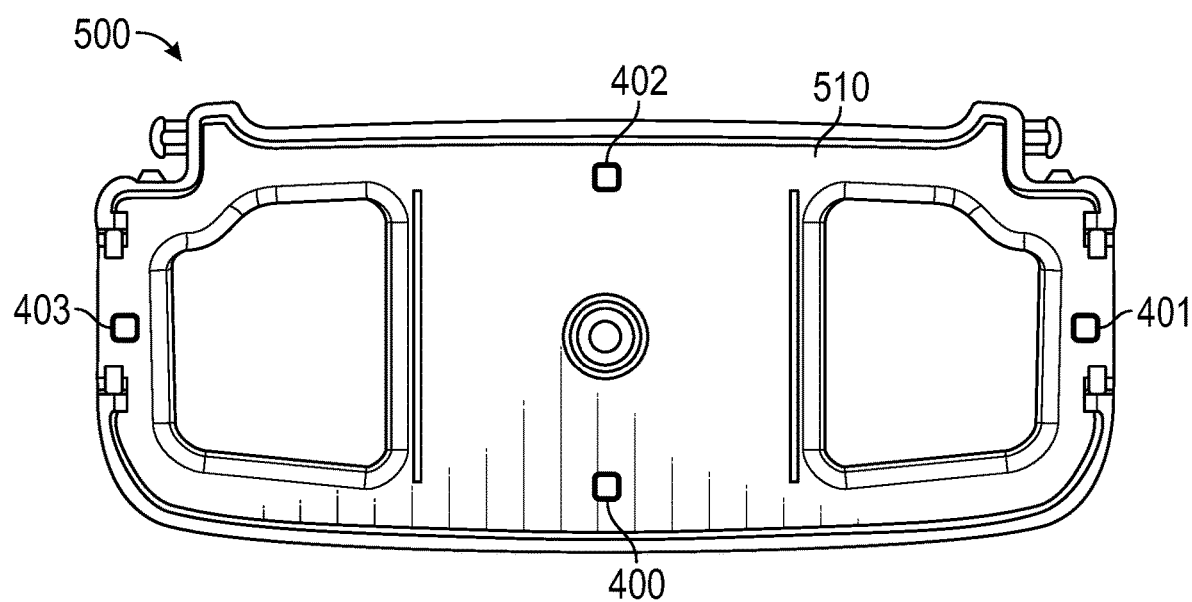
Figure 5C:
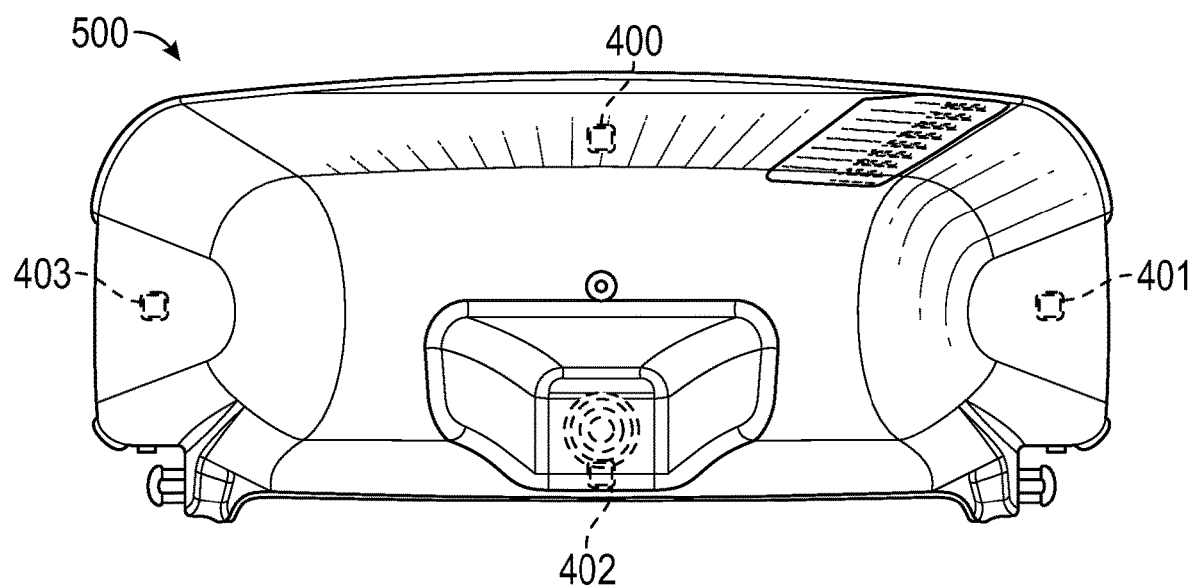
Figure 5D:
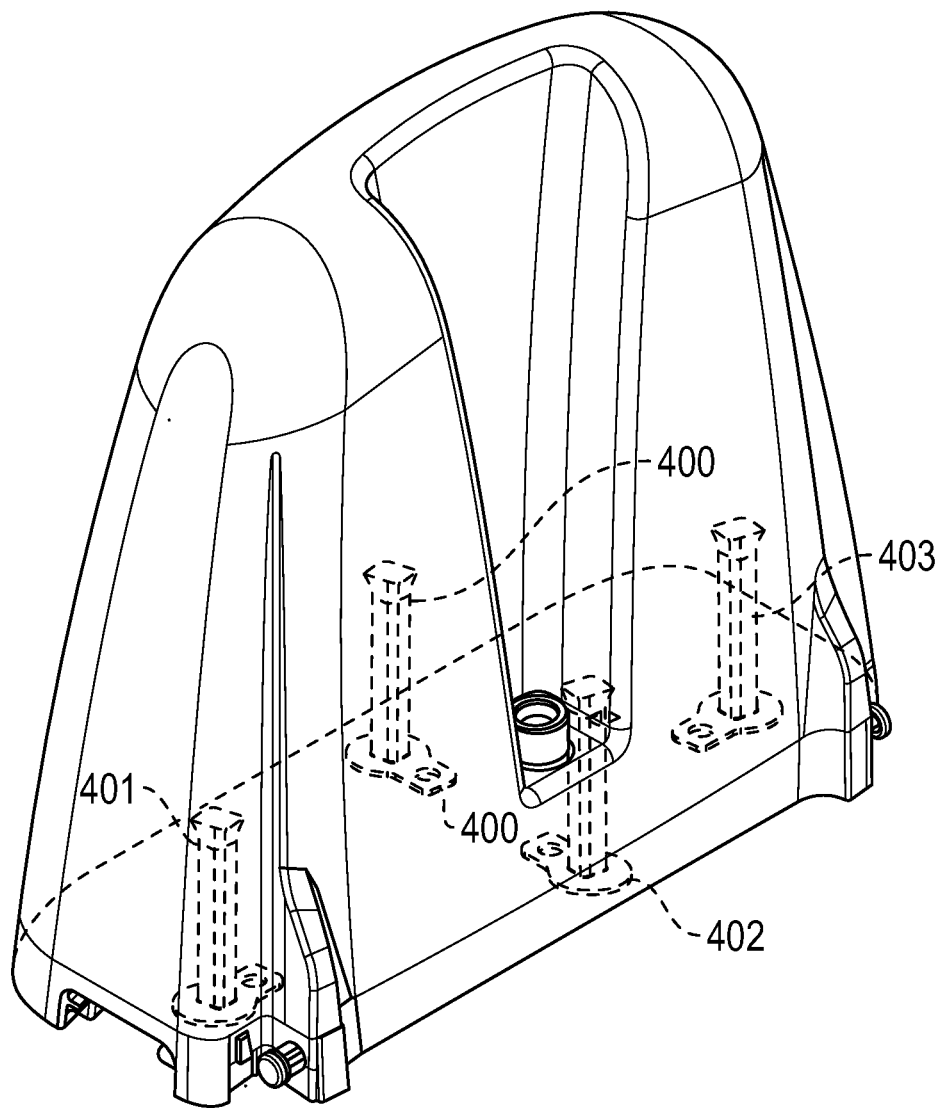
Figure 5E:
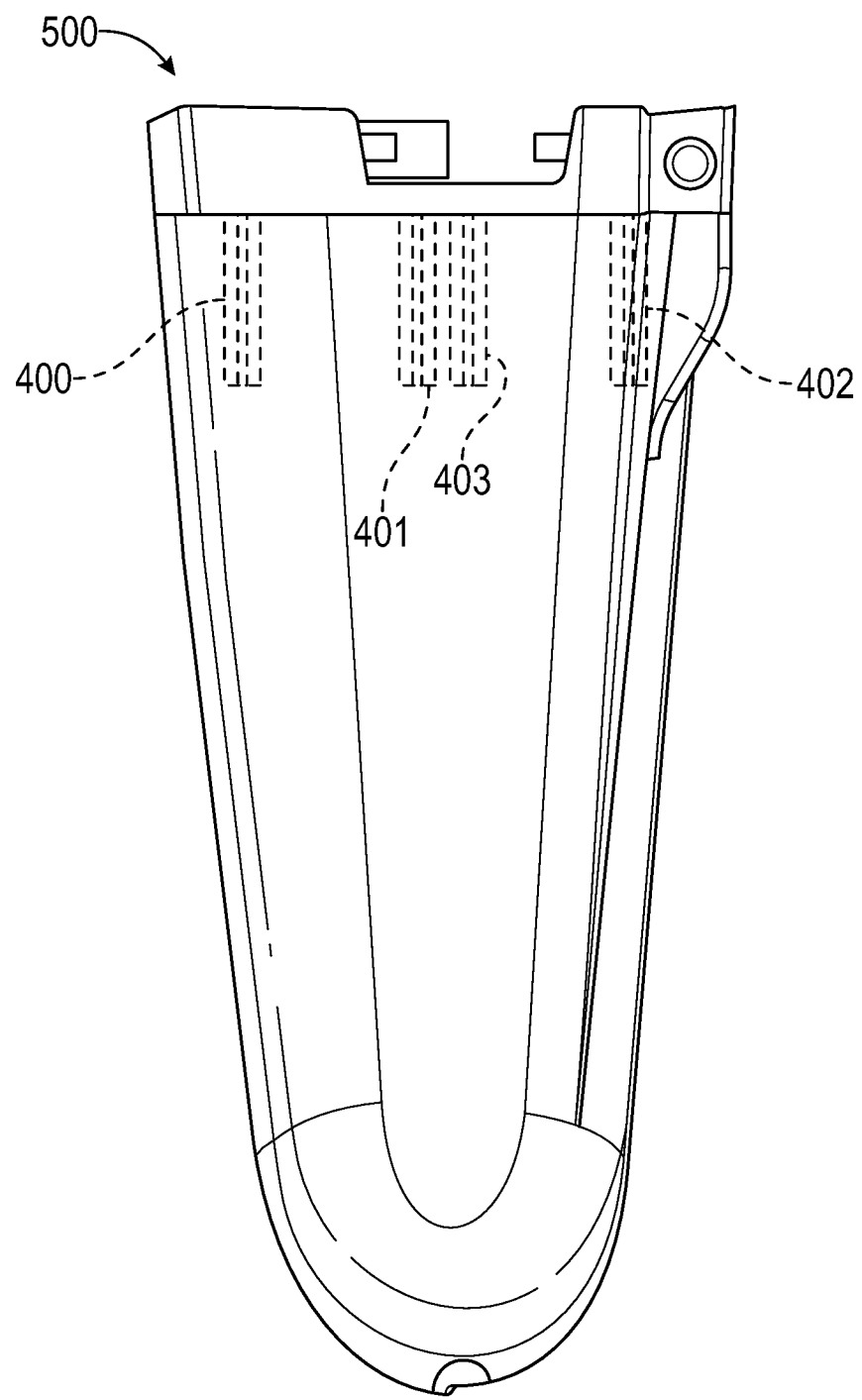
Figure 6A:
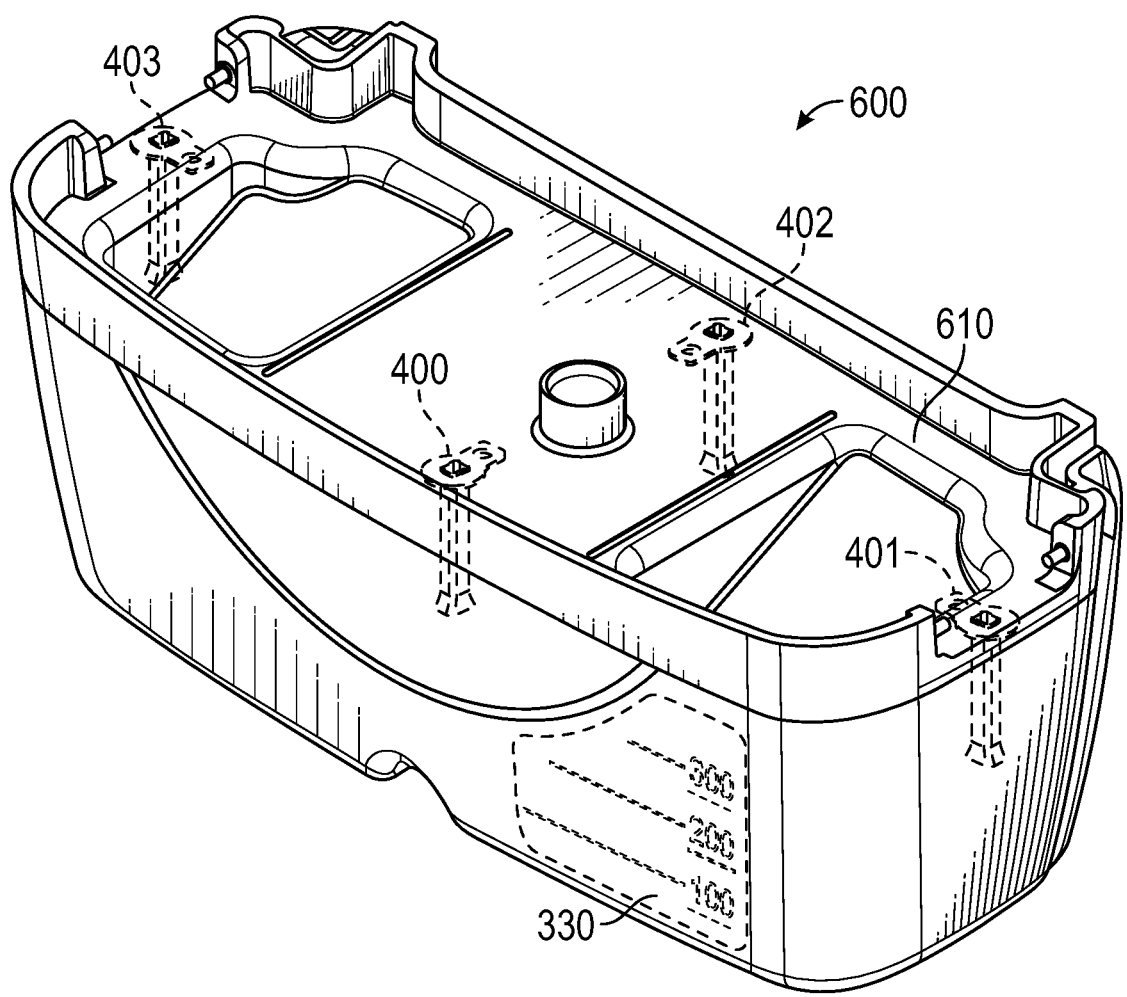
Figure 6B:
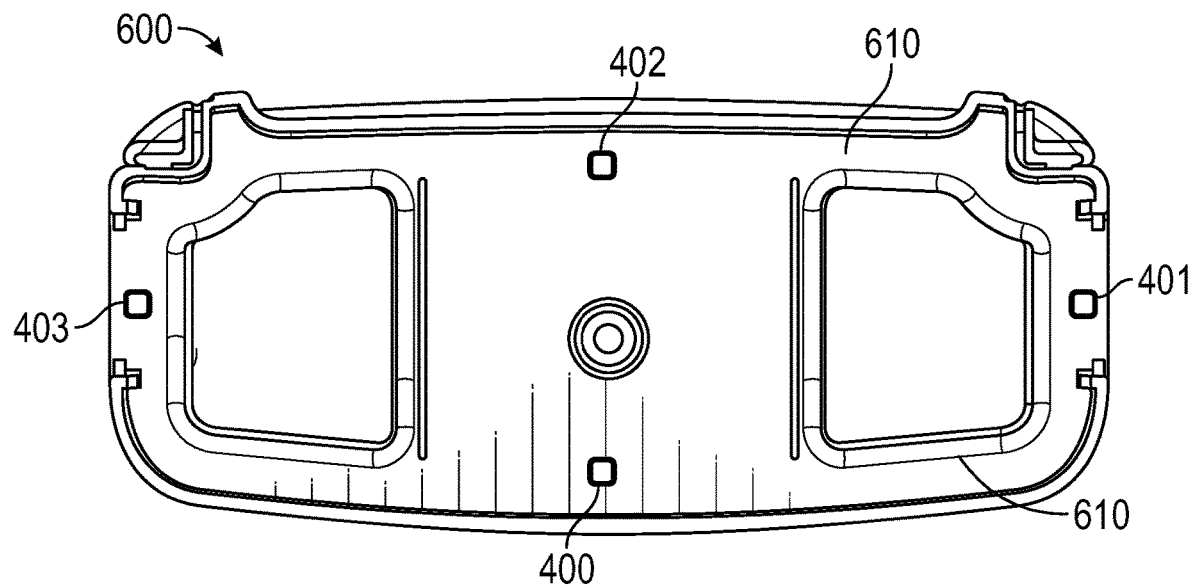
Figure 6C:
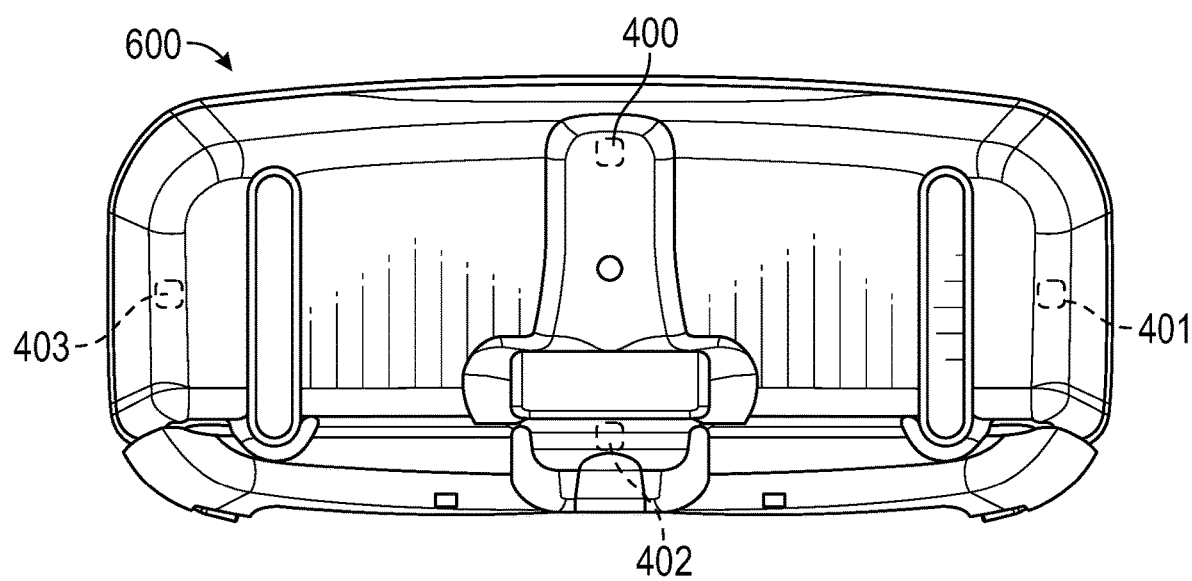
Figure 6D:
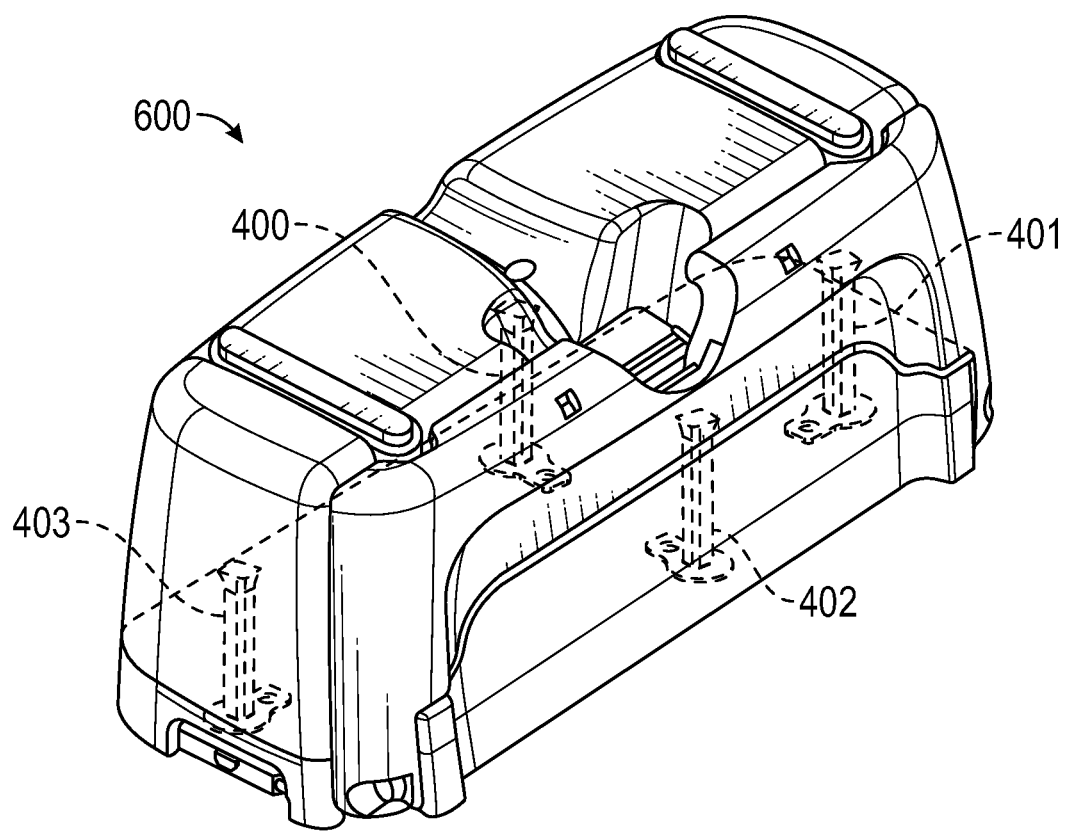
Figure 6E:
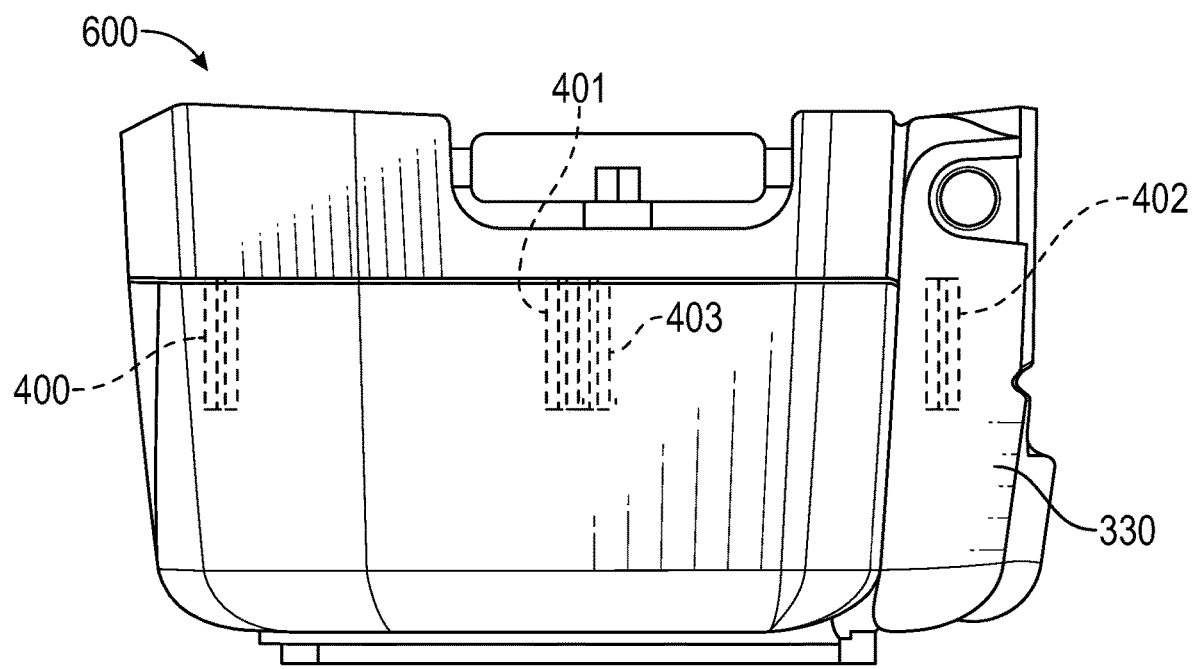
Figure 7A:
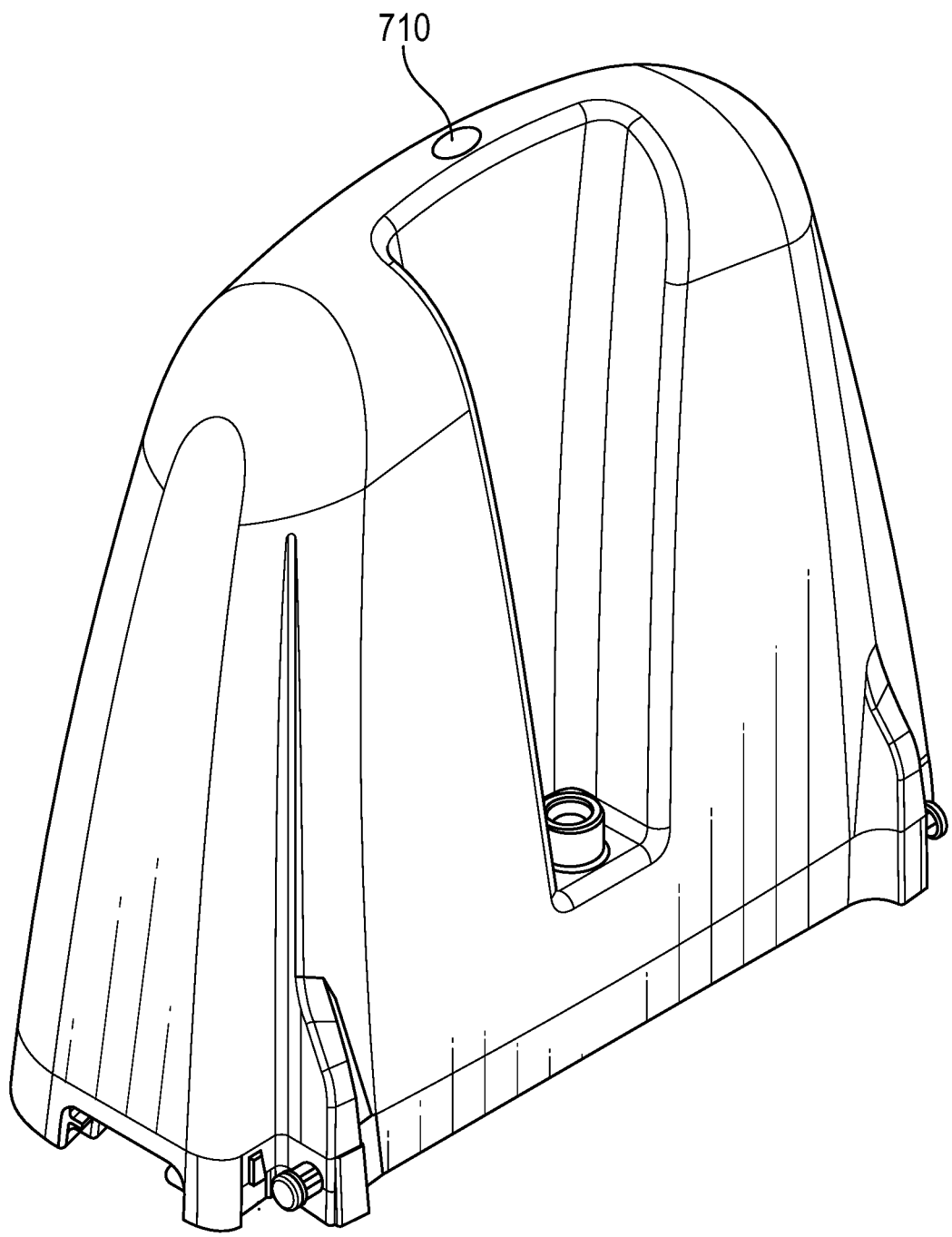
FIGS. 7A-7B and 8A-8B illustrate canisters with light sources according to some embodiments.
Figure 7B:
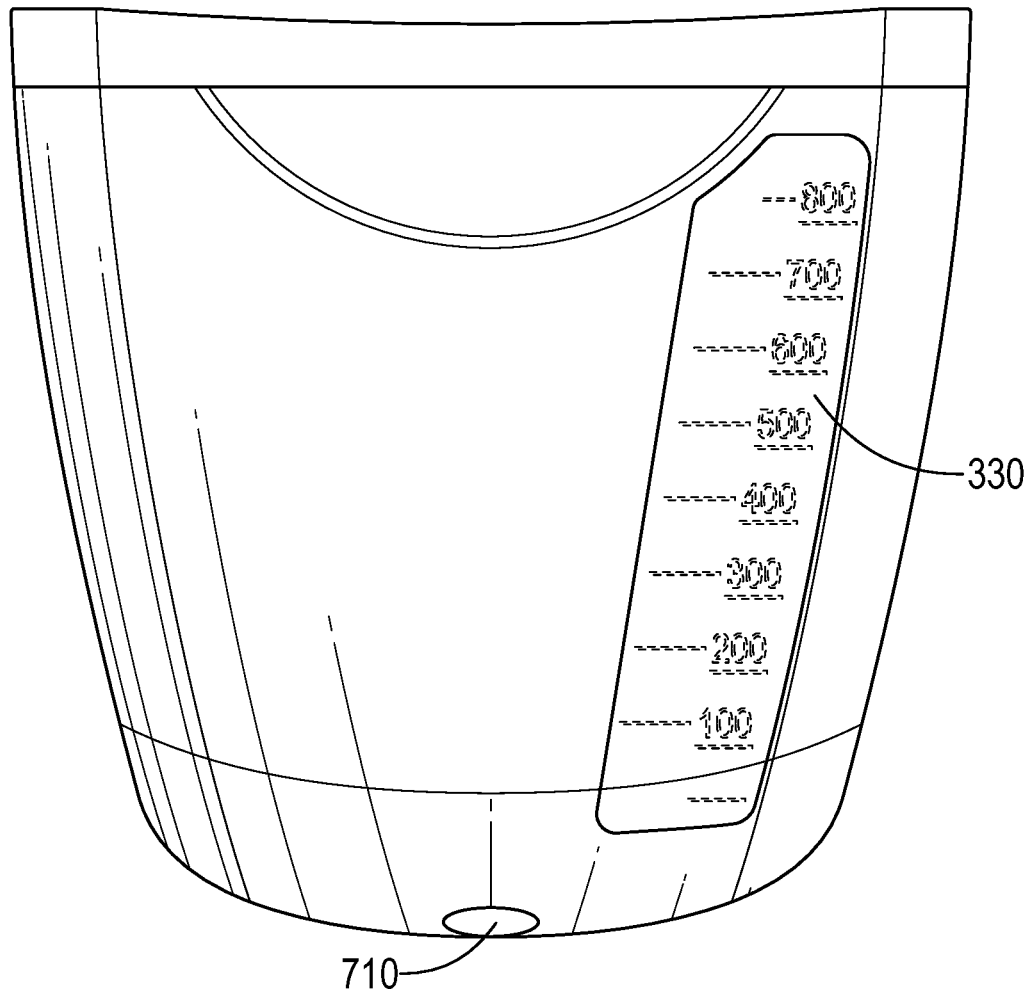
Figure 8A:
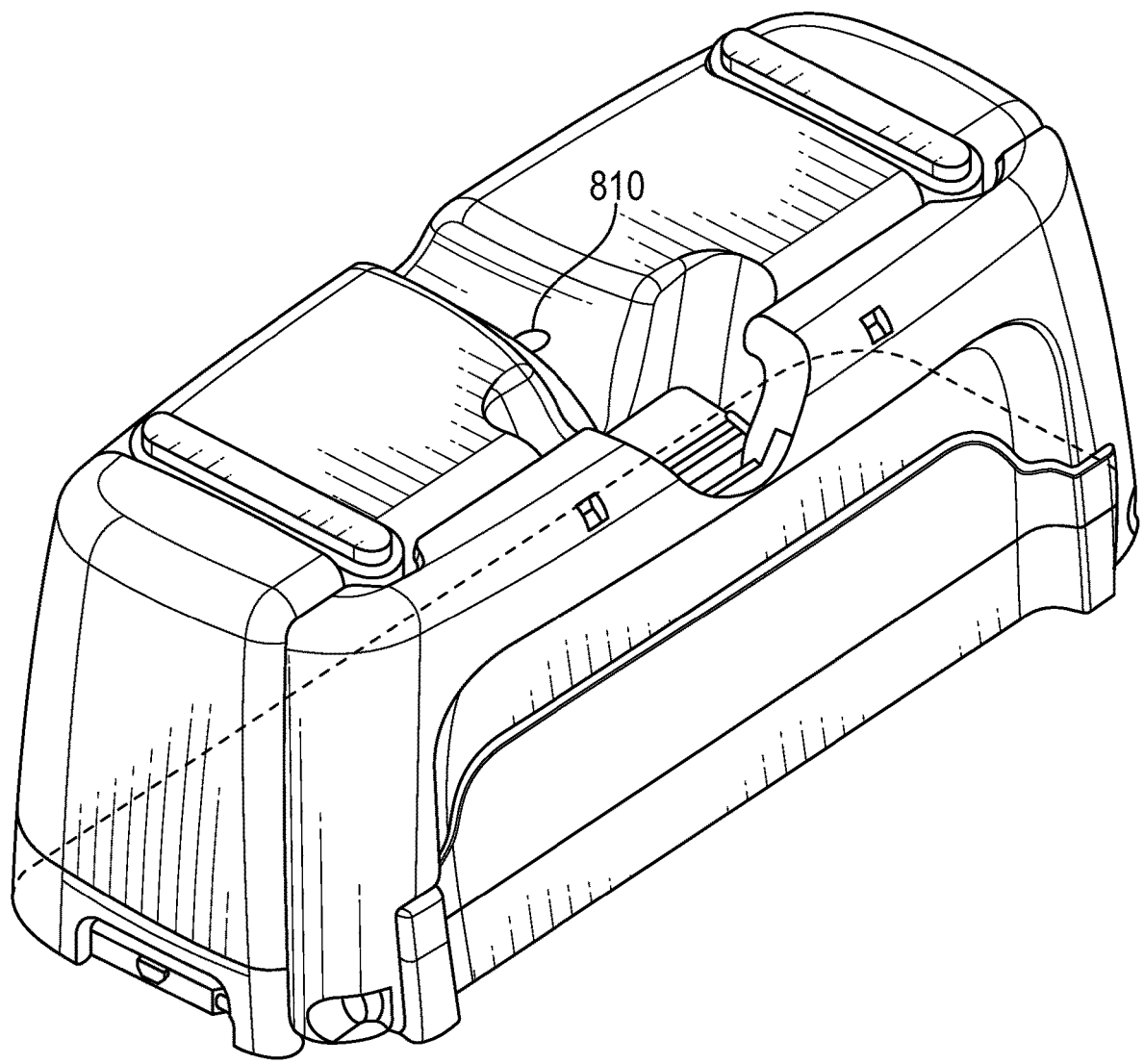
Figure 8B:
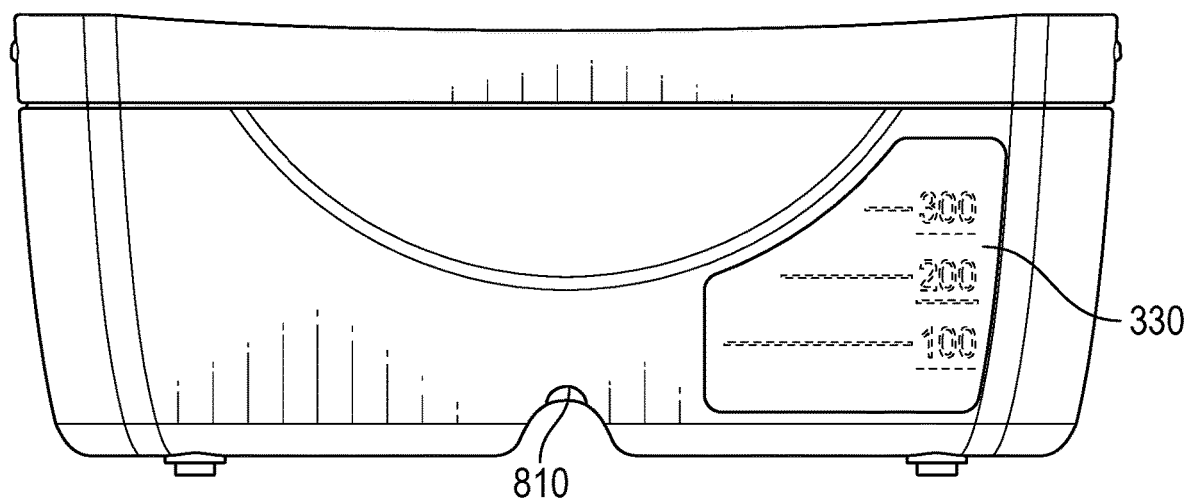

FIGS. 5A-5E illustrate of how one or more light pipes 400, 401, 402, and 403 can be positioned in a large canister 500. FIG. 5A illustrates a prospective top side view of the canister 500. As illustrated, four light pipes 400403, which can match the layout of light sources illustrated in FIG. 2B, can be positioned on the top surface 510 of the canister. When the canister 500 is attached to the device housing 200, the bottom surface 217 of the device housing comes in contact with the tope surface 510 of the canister. FIG. 5B illustrates a top view of the canister top 510 with positioning of the light pipes 400-403 on the top surface 510. FIG. 5C illustrates a bottom view of the bottom of the canister 500 illustrating locations where the light pipes terminate, such as via the exit potion 440 as described herein. FIG. 5D illustrate a prospective bottom side view illustrating how the light pipes 400-403 are positioned in the canister 510. FIG. 5E shows a side view of the canister 510 illustrating positioning of the light pipes. The light entrance 410 (not shown) of the light pipes 400-403 can be flush with the large canister top 510 as to provide an intimate interface between the LEDs located on the device housing. The light entrance 410 of light pipes 400-403 can protrude above the top surface 510 or be indented below the top surface 510 to better provide contact with the corresponding light source positioned on the bottom surface 217 of the device housing 200. Corresponding light pipe arrangements reflecting the LED placements in FIG. 2B-2D can also be used. Each of the light pipes 400-403 can be of a suitable shape, length, or the like depending on its positioning in the canister.

FIGS. 6A-6E illustrate how one or more light pipes 400, 401, 402, and 403 can be positioned in small canister 600. The illustrated embodiments are similar to those described herein in connection with FIGS. 5A-5E.

Additionally or alternatively, one or more light sources can be positioned in the canister. FIGS. 7A-7B and 8A-8B show placement of one or more light sources 710 or 810 in the canisters. One or more light sources can be LEDs, such as round LEDs that provide improved diffusion of light. In some cases, one or more light sources 710 or 810 can be used instead of the one or more light sources 220, 221, 222, 223 positioned on the device housing 200. One or more light sources 710 or 810 can be used in conjunction with the one or more light sources 220, 221, 222, 223 positioned on the device housing 200. As illustrated in FIGS. 7A-7B and 8A-8B, one or more light sources 710 or 810 can be placed on the bottom of the canisters.

Multiple light sources can also be used and placed in the canisters. For example, light sources can be placed along the sides of the canisters. Light sources can be controlled by the NPWT device, such as by the controller, and can receive control signals from the device housing, such as via the controller, via wireless or physical transmission. For example, one or more wires can be run through channels formed in the canister surfaces. The one or more light sources can be positioned so as to be with electrical communication at the canister top. When the canister is connected to the device housing 200, a connector on the bottom surface 217 can contact the connection at the canister top to complete the electrical circuit. The one or more light sources 710 or 810 can be independently powered or be powered by the NPWT device.

In some cases, a separate light source panel layer can also be placed between the device housing 200 and the canister to provide illumination. This panel can serve as a light source. This panel can serve as a power source for the light source. The light sources of the panel, such as LEDs, OLEDs, luminescent backlights, electro-luminescent back panels of OLED panels, or the like, can be placed along the four edges of the bottom surface of the panel. The light sources can additionally or alternatively be placed in the midline of panel. The panel can also have a single light source. Uses of the single light source can necessitate a strong intensity light source, however all types of light sources with different intensities can be used. The light sources of the panels can be aligned with the light pipes as described herein.

In some cases, the canister can be used as a user interface to provide various indications to the user. For example, the NPWT system can detect and the canister can visually indicate that the patient is walking, standing, sitting, or the like. A highly efficient system can be provided whereby the user can rapidly verify status of parameters and the canister can function as a user interface.

Disclosed embodiments can provide the user or a caregiver with a system that gives simple, quick and accurate feedback to describe the status of the NPWT system, patient activity, or the like. The use of the canister as a source of visual indication can allow the user to determine or verify the status of the system quickly and reliably even from a distance.

Terminology

Many other variations than those described herein will be apparent from this disclosure. For example, depending on the embodiment, certain acts, events, or functions of any of the steps described herein can be performed in a different sequence, can be added, merged, or left out altogether (e.g., not all described acts or events are necessary for the practice of the algorithms). Moreover, in certain embodiments, acts or events can be performed concurrently. In addition, different tasks or processes can be performed by different machines and/or computing systems that can function together. While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy apparatus comprising:
   a device housing enclosing:
      a negative pressure source configured to provide negative pressure via a fluid flow path to a wound covered by a wound dressing, and
      a controller configured to determine a plurality of conditions associated with provision of negative pressure wound therapy by the negative pressure source, the controller further configured to cause provision of a plurality of visual indications associated with the plurality of conditions to a user;
   a canister configured to be attached to the device housing and further configured to be fluidically connected to the negative pressure source, the canister comprising a canister housing including one or more exterior surfaces defining an interior volume that is configured to store at least some fluid removed from the wound; and
   at least one light pipe comprising a light entrance positioned along an exterior surface of the one or more exterior surfaces of the canister and a light exit positioned entirely in the interior volume of the canister, the at least one light pipe configured to transmit light associated with a visual indication of the plurality of visual indications through at least a portion of the interior volume, thereby causing the provision of the visual indication to the user via the canister.

2. The apparatus of claim 1, further comprising at least one light source supported by the device housing and positioned at least partially on a device housing surface configured to face the interior volume of the canister when the canister is attached to the device housing, wherein the light entrance of the at least one light pipe at least partially coincides with a location of the at least one light source on the device housing surface when the canister is attached to the device housing.

3. The apparatus of claim 1, wherein the at least one light pipe is positioned in the interior volume of the canister proximal to the one or more exterior surfaces of the canister.

4. The apparatus of claim 3, wherein the at least one light pipe comprises a plurality of light pipes positioned in the interior volume of the canister proximal to the one or more exterior surfaces of the canister.

5. The apparatus of claim 1, wherein the plurality of conditions comprises at least two of normal operation, blockage, canister full, leak, high pressure, or presence of blood.

6. The apparatus of claim 1, wherein the plurality of visual indications comprises at least two of green illumination, yellow illumination, or red illumination.

7. A method of providing a visual indication to a user of a negative pressure wound therapy apparatus, the method comprising:
   by a controller of the negative pressure wound therapy apparatus, determining a plurality of conditions associated with provision of negative pressure wound therapy by a negative pressure source of the negative pressure wound therapy apparatus and causing provision of a plurality of visual indications associated with the plurality of conditions to a user; and
   by at least one light pipe comprising a light entrance positioned along an exterior surface of one or more exterior surfaces of a canister of the negative pressure wound therapy apparatus and a light exit positioned entirely in an interior volume of the canister, transmitting light associated with at least a first visual indication of the plurality of visual indications through at least a portion of the interior volume of the canister or by at least one light source positioned in the interior volume of the canister, providing at least a second visual indication of the plurality of visual indications, wherein the interior volume of the canister continuously extends entirely along top and bottom sides of the canister and is configured to store at least some fluid aspirated by the negative pressure source.

8. The method of claim 7, wherein the interior volume of the canister is defined by the one or more exterior surfaces of the canister, and wherein the at least one light pipe comprises a plurality of light pipes positioned proximally to opposing one or more exterior surfaces of the canister.

9. The method of claim 7, wherein the at least one light source is positioned proximally to one or more of: a surface of the canister or a portion of a transparent surface of the canister, wherein the transparent surface of the canister comprises a polished surface.

10. The apparatus of claim 1, further comprising at least one light source positioned in the interior volume of the canister and configured to provide the visual indication to the user via the canister.

11. The method of claim 7, comprising:
   by the at least one light pipe, transmitting light associated with at least the first visual indication through at least the portion of the interior volume of the canister; and
   by the at least one light source positioned in the interior volume of the canister, providing at least the second visual indication.

12. The apparatus of claim 1, further comprising a light panel separate from the device housing and the canister, the light panel configured to be positioned between the device housing and the canister and further configured to provide the light associated with the visual indication to the at least one light pipe.

13. The apparatus of claim 2, wherein:
   the at least one light source comprises a detector configured to determine that the at least one light pipe is engaged responsive to a determination that the at least one light pipe is positioned within a threshold distance or orientation with respect to the at least one light source, and the controller is further configured to cause the negative pressure source to provide negative pressure to the wound responsive to a determination that the at least one light pipe is engaged; and
   the detector is configured to determine that the at least one light pipe is not engaged responsive to a determination that the at least one light pipe is not positioned within the threshold distance or orientation with respect to the at least one light source, and the controller is further configured prevent the negative pressure source from providing negative pressure to the wound responsive to a determination that the at least one light pipe is not engaged.

* * * * *